US008872941B2

(12) United States Patent
Asukai et al.

(10) Patent No.: US 8,872,941 B2
(45) Date of Patent: Oct. 28, 2014

(54) IMAGING APPARATUS AND IMAGING METHOD

(75) Inventors: Masamichi Asukai, Kanagawa (JP); Masaaki Tsuruta, Tokyo (JP); Taiji Ito, Kanagawa (JP); Kan Ebisawa, Kanagawa (JP); Yoichiro Sako, Tokyo (JP)

(73) Assignee: Sony Corporation, Tokyo (JP)

( * ) Notice: Subject to any disclaimer, the term of this patent is extended or adjusted under 35 U.S.C. 154(b) by 599 days.

(21) Appl. No.: 11/977,349

(22) Filed: Oct. 24, 2007

(65) Prior Publication Data
US 2008/0129839 A1    Jun. 5, 2008

(30) Foreign Application Priority Data
Nov. 7, 2006   (JP) .................. 2006-301600

(51) Int. Cl.
*H04N 5/76* (2006.01)
*H04N 5/225* (2006.01)
*H04N 5/232* (2006.01)
*A61B 3/113* (2006.01)
*G02B 27/01* (2006.01)
*A61B 5/00* (2006.01)

(52) U.S. Cl.
CPC ......... *H04N 5/23293* (2013.01); *H04N 5/2251* (2013.01); *A61B 3/113* (2013.01); *G02B 2027/0138* (2013.01); *G02B 27/017* (2013.01); *A61B 5/00* (2013.01); *G02B 2027/0187* (2013.01); *G02B 2027/014* (2013.01)
USPC .................................................... 348/231.99

(58) Field of Classification Search
USPC ........ 348/61, 63, 151, 211, 212, 214, 231.99, 348/273–276; 345/156, 327; 382/114; 350/298; 145/327; 396/111
See application file for complete search history.

(56) References Cited

U.S. PATENT DOCUMENTS

| | | | |
|---|---|---|---|
| 6,091,546 A * | 7/2000 | Spitzer | 359/618 |
| 6,181,371 B1 | 1/2001 | Maguire, Jr. | |
| 6,466,862 B1 | 10/2002 | Dekock et al. | |
| 6,549,231 B1 * | 4/2003 | Matsui | 348/61 |

(Continued)

FOREIGN PATENT DOCUMENTS

| | | |
|---|---|---|
| CN | 1605974 A | 4/2005 |
| CN | 1835711 A | 9/2006 |

(Continued)

OTHER PUBLICATIONS

Healey, Jennifer et al.: "StartleCam: A Cybernetic Wearable Camera,". Digest of Papers. Second International Symposium on Wearable Computers, 1998 Pittsburgh, PA USA Oct. 1920, 1998, pp. 42-49.

*Primary Examiner* — Roberto Velez
*Assistant Examiner* — Tuan Le
(74) *Attorney, Agent, or Firm* — Wolf, Greenfield & Sacks, P.C.

(57) ABSTRACT

Disclosed herein is an imaging apparatus including: imaging means for imaging a scene that is in a direction in which a user sees to obtain image data of the scene; temporary storage means for storing the image data obtained by imaging by the imaging means; and control means for controlling the temporary storage means to store the image data obtained by imaging by the imaging means, and, when a predetermined storage condition has been satisfied, extracting image data to be stored from the temporary storage means and adding metadata to the extracted image data to perform a storage process.

43 Claims, 16 Drawing Sheets

(56) References Cited

U.S. PATENT DOCUMENTS

| | | |
|---|---|---|
| 6,629,104 B1 * | 9/2003 | Parulski et al. ............... 382/307 |
| 7,183,909 B2 | 2/2007 | Miyajima |
| 7,286,753 B2 * | 10/2007 | Yamasaki ....................... 396/51 |
| 7,876,374 B2 | 1/2011 | Sako et al. |
| 7,925,029 B2 * | 4/2011 | Hollemans et al. ............. 381/74 |
| 7,928,395 B2 * | 4/2011 | Grimberg ..................... 250/349 |
| 8,009,219 B2 | 8/2011 | Sako et al. |
| 2001/0005230 A1 * | 6/2001 | Ishikawa ................... 348/333.03 |
| 2001/0040590 A1 | 11/2001 | Abbott et al. |
| 2002/0054174 A1 | 5/2002 | Abbott et al. |
| 2002/0128541 A1 * | 9/2002 | Kim et al. ..................... 600/301 |
| 2003/0011684 A1 | 1/2003 | Narayanaswami et al. |
| 2003/0108241 A1 | 6/2003 | Colmenarez et al. |
| 2003/0117505 A1 | 6/2003 | Sasaki et al. |
| 2003/0165269 A1 | 9/2003 | Fedorovskaya et al. |
| 2003/0225516 A1 | 12/2003 | DeKock et al. |
| 2003/0235411 A1 * | 12/2003 | Morikawa et al. ............ 396/281 |
| 2004/0070563 A1 * | 4/2004 | Robinson ..................... 345/156 |
| 2004/0101212 A1 * | 5/2004 | Fedorovskaya et al. ...... 382/305 |
| 2004/0119840 A1 | 6/2004 | Ishihara et al. |
| 2004/0155968 A1 * | 8/2004 | Cheatle et al. ........... 348/207.99 |
| 2004/0174443 A1 | 9/2004 | Simske |
| 2004/0267440 A1 | 12/2004 | Dekock et al. |
| 2005/0195277 A1 * | 9/2005 | Yamasaki ....................... 348/61 |
| 2005/0206583 A1 * | 9/2005 | Lemelson et al. ................. 345/7 |
| 2005/0231599 A1 | 10/2005 | Yamasaki |
| 2005/0248469 A1 | 11/2005 | Dekock et al. |
| 2005/0248852 A1 * | 11/2005 | Yamasaki ..................... 359/630 |
| 2005/0250996 A1 | 11/2005 | Shirai et al. |
| 2006/0012690 A1 * | 1/2006 | Nakamura et al. ......... 348/231.6 |
| 2006/0074546 A1 | 4/2006 | Dekock et al. |
| 2006/0115130 A1 | 6/2006 | Kozlay |
| 2006/0203998 A1 * | 9/2006 | Ben-Arie ..................... 379/430 |
| 2006/0217598 A1 | 9/2006 | Miyajima et al. |
| 2006/0268330 A1 * | 11/2006 | Takanezawa ................ 358/1.15 |
| 2007/0116450 A1 * | 5/2007 | Kijima ......................... 396/111 |
| 2007/0162505 A1 | 7/2007 | Cecchi et al. |
| 2008/0107361 A1 | 5/2008 | Asukai et al. |
| 2008/0136930 A1 | 6/2008 | Nagai |
| 2008/0253695 A1 | 10/2008 | Sano et al. |
| 2008/0259199 A1 | 10/2008 | Sako et al. |
| 2009/0040231 A1 | 2/2009 | Sano et al. |
| 2010/0063997 A1 | 3/2010 | Sako et al. |
| 2010/0220037 A1 | 9/2010 | Sako et al. |

FOREIGN PATENT DOCUMENTS

| | | |
|---|---|---|
| EP | 1246136 A2 | 3/2002 |
| EP | 1 324 274 A2 | 7/2003 |
| EP | 1324274 A2 | 7/2003 |
| EP | 1503376 A | 2/2005 |
| EP | 1571634 A1 | 2/2005 |
| EP | 1522256 A1 | 4/2005 |
| EP | 1593964 A | 11/2005 |
| EP | 1656880 A | 5/2006 |
| EP | 1708150 A | 10/2006 |
| GB | 2394852 A | 5/2004 |
| GB | 2 403 365 A | 12/2004 |
| GB | 2403366 A | 12/2004 |
| JP | 9-65188 A | 3/1997 |
| JP | 10-113343 A | 5/1998 |
| JP | 2000-285221 A | 10/2000 |
| JP | 2001-036800 A | 2/2001 |
| JP | 2002-169809 A | 6/2002 |
| JP | 2003-079591 A | 3/2003 |
| JP | 2003-204464 A | 7/2003 |
| JP | 2004-049309 A | 2/2004 |
| JP | 2004-178593 A | 6/2004 |
| JP | 2004-194996 A | 7/2004 |
| JP | 2004-537193 A | 12/2004 |
| JP | 2004-538679 A | 12/2004 |
| JP | 2004-538681 A | 12/2004 |
| JP | 2005-064839 A | 3/2005 |
| JP | 2005-080000 A | 3/2005 |
| JP | 2005-124909 A | 5/2005 |
| JP | 2005-141281 A | 6/2005 |
| JP | 2005-172851 A | 6/2005 |
| JP | 2005-195425 A | 7/2005 |
| JP | 2005-250977 A | 9/2005 |
| JP | 2005-260892 A | 9/2005 |
| JP | 2005-337863 A | 12/2005 |
| JP | 2005-341604 A | 12/2005 |
| JP | 2006-034803 A | 2/2006 |
| JP | 2006-080644 A | 3/2006 |
| JP | 2006-080651 A | 3/2006 |
| JP | 2006-086823 A | 3/2006 |
| JP | 2006-087829 A | 4/2006 |
| JP | 2006-098827 A | 4/2006 |
| JP | 2006-126891 A | 5/2006 |
| JP | 2006-146630 A | 6/2006 |
| JP | 2006-172146 A | 6/2006 |
| JP | 2006-279764 A | 10/2006 |
| JP | 2007-011391 A | 1/2007 |
| JP | 2007-041964 A | 2/2007 |
| JP | 2007-081681 A | 3/2007 |
| WO | WO 99/49656 A | 9/1999 |
| WO | WO 01/43104 A1 | 6/2001 |
| WO | WO 2004/017249 A2 | 2/2004 |

* cited by examiner

SEE-THROUGH

IMAGE OBTAINED BY REGULAR IMAGING

TELEPHOTO IMAGE

IMAGE OBTAINED BY REGULAR IMAGING

MAGNIFIED IMAGE

IMAGE OBTAINED BY REGULAR IMAGING

WITH INCREASED INFRARED SENSITIVITY

IMAGE OBTAINED BY REGULAR IMAGING

WITH INCREASED ULTRAVIOLET SENSITIVITY

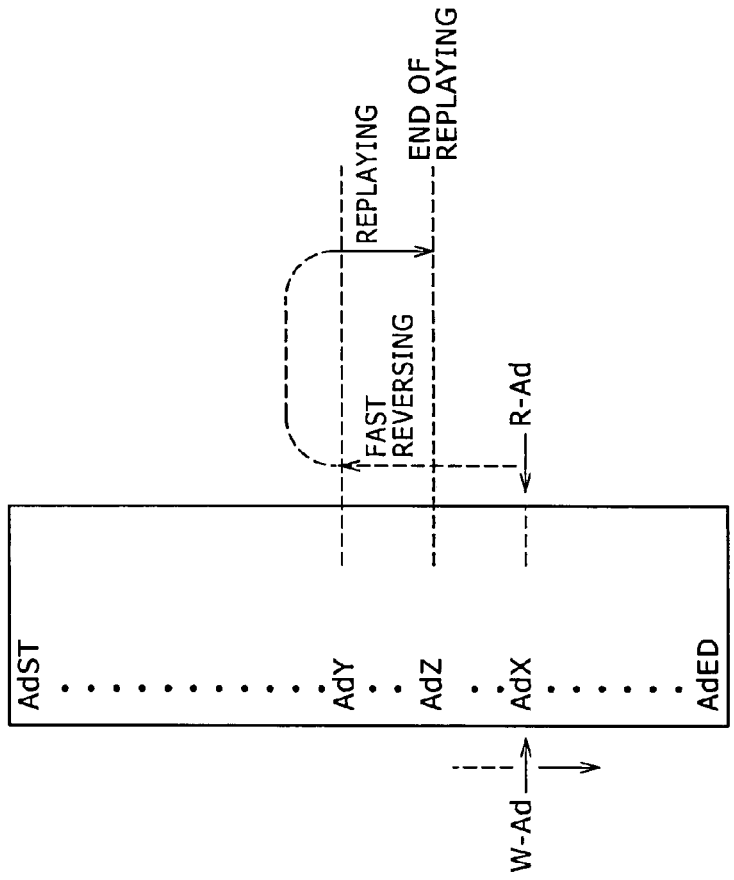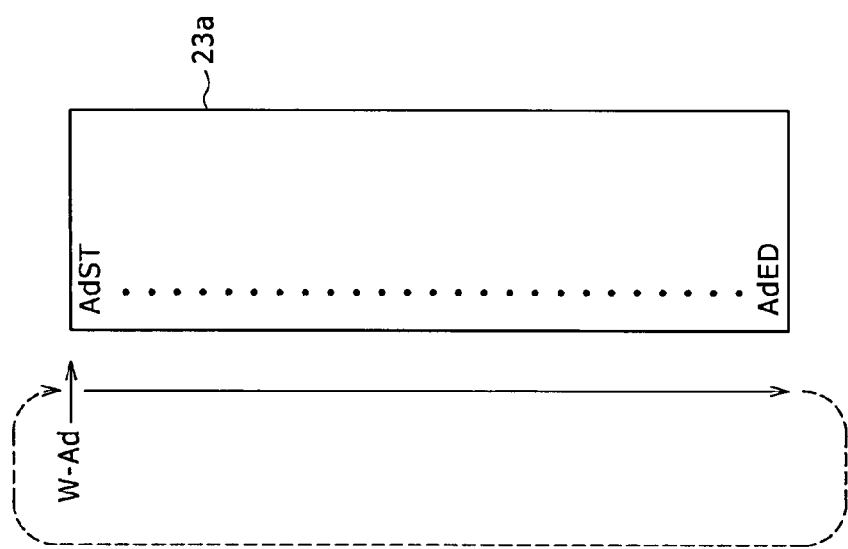

IMAGING APPARATUS AND IMAGING METHOD

CROSS REFERENCES TO RELATED APPLICATIONS

The present invention contains subject matter related to Japanese Patent Application JP 2006-301600 filed in the Japan Patent Office on Nov. 7, 2006, the entire contents of which being incorporated herein by reference.

BACKGROUND OF THE INVENTION

1. Field of the Invention

The present invention relates to an imaging apparatus and method for image a scene that is in a direction in which a user sees while the imaging apparatus is worn by the user using, for example, a spectacle-shaped or head-worn wearing unit.

2. Description of the Related Art

There has been proposed an apparatus that has a spectacle-shaped or head-worn wearing unit to which a small camera is attached so as to be able to image a scene that is in the direction in which the user sees (see, for example, Japanese Patent Laid-Open No. 2005-172851).

SUMMARY OF THE INVENTION

The capability to image the scene that is in the direction in which the users sees allows a scene that the user sees in his or her daily life to be recorded as image data, for example, but no known apparatus is capable of allowing the image data obtained by imaging to be used in a mode desirable for the user.

As such, the present invention has been devised to enable appropriate storage and easy replaying of a photographed image.

According to one embodiment of the present invention, there is provided an imaging apparatus including: an imaging section configured to image a scene that is in a direction in which a user sees to obtain image data of the scene; a temporary storage section configured to store the image data obtained by imaging by the imaging section; and a control section configured to control the temporary storage section to store the image data obtained by imaging by the imaging section, and, when a predetermined storage condition has been satisfied, extracting image data to be stored from the temporary storage section and adding metadata to the extracted image data to perform a storage process.

The temporary storage section may use a storage area in a ring memory manner to store the image data continuously.

Also, the imaging apparatus may further include storage section for storing data in a nonvolatile storage medium, wherein as the storage process, the control section performs a process of controlling the storage section to store the image data extracted from the temporary storage section and the metadata in the nonvolatile storage medium.

Also, the imaging apparatus may further include a transmission section configured to transmit data to an external device, wherein as the storage process, the control section performs a process of controlling the transmission section to transmit the image data extracted from the temporary storage section and the metadata to the external device.

Also, the imaging apparatus may further include a display section capable of performing image display (e.g., display of replay images) using the image data stored in the temporary storage section.

The display section may be capable of causing a whole or a part of a screen area for image display to enter a transparent or translucent see-through state. In this case, the control section may control the display section to cause a part of the screen area for image display to enter the see-through state, while performing image display using the image data stored in the temporary storage section with a remaining part of the screen area.

Also, the control section may control the display section to perform image display using the image data being obtained by imaging by the imaging section with a part of a screen area for image display, while performing image display using the image data stored in the temporary storage section with a remaining part of the screen area.

Also, the display section may be arranged in front of an eye of the user to perform image display.

Also, the display section may be formed in a different case from a case that contains the imaging section.

Also, the imaging apparatus may further include an operation input section, wherein in accordance with an operation input by the user detected by the operation input section, the control section controls the display section to perform image display using the image data stored in the temporary storage section.

The operation input section may include an operation unit to be operated by the user.

Also, the operation input section may include a sensor for detecting a motion of the user.

Also, the operation input section may include a sensor for detecting biological information concerning the user.

When the display section has performed image display (e.g., display of the replay images) using the image data stored in the temporary storage section, the control section may determine that the storage condition has been satisfied, and extract, as the image data to be stored, all or some of the image data displayed from the temporary storage section and add the metadata to the extracted image data to perform the storage process.

Also, the imaging apparatus may further include a biological sensor section configured to detect biological information concerning the user, wherein the control section determines based on the biological information detected by the biological sensor section whether the storage condition has been satisfied, and when the control section has determined that the storage condition has been satisfied, the control section extracts the image data to be stored from the temporary storage section and adds the metadata to the extracted image data to perform the storage process. The biological information may be at least one of a pulse, heart beats, an electrocardiogram, electromyographic information, breathing, perspiration, GSR (galvanic skin response), blood pressure, a saturation oxygen concentration in blood, a skin surface temperature, brain waves, a blood flow change, a body temperature, a motion of a body, a motion of a head, a center of gravity, rhythm of walking/running, and a state of an eye.

Also, the imaging apparatus may further include: an audio input section configured to input external sound; and an audio analysis section configured to analyze an audio signal obtained by the audio input section, wherein the control section determines based on a result of analysis by the audio analysis section whether the storage condition has been satisfied, and when the control section has determined that the storage condition has been satisfied, the control section extracts the image data to be stored from the temporary storage section and adds the metadata to the extracted image data to perform the storage process.

Also, the control section may perform imaging system control of issuing an instruction related to imaging by the imaging section or processing on the image data obtained by imaging, and when the control section has performed predetermined imaging system control, the control section may determine that the storage condition has been satisfied, and extract the image data to be stored from the temporary storage section and add the metadata to the extracted image data to perform the storage process. For example, the control section may determine that the storage condition has been satisfied when, as the imaging system control, the control section has performed control of causing a lens system in the imaging section to perform a predetermined operation, control of causing a signal processing system in the imaging section to perform a predetermined process, control of changing imaging sensitivity in the imaging section, control of changing a frame rate in the imaging section, or the like.

Also, when the storage condition has been satisfied, the control section may generate the metadata in accordance with the satisfied storage condition.

According to another embodiment of the present invention, there is provided an imaging method including the steps of: (a) imaging a scene that is in a direction in which a user sees to obtain image data of the scene; (b) temporarily storing the image data obtained by imaging in step (a); (c) determining whether a predetermined storage condition has been satisfied; and (d) when step (c) has determined that the predetermined storage condition has been satisfied, extracting image data to be stored from the image data temporarily stored in step (b), adding metadata to the extracted image data, and performing a storage process.

According to the above-described embodiments of the present invention, the user wears the imaging apparatus using a spectacle-shaped or head-worn wearing unit, for example, so that the imaging section is able to image the scene that is in the direction in which the user sees. The imaging section is configured to perform imaging constantly and continuously, for example, and the image data obtained by imaging is sequentially stored in the temporary storage section in the ring memory manner, for example. Because the image data constantly obtained by imaging is stored in the temporary storage section, photographed image data corresponding to a time period from the current time to a time in the past, which depends on the capacity of the temporary storage section, is stored temporarily.

The image data stored in the temporary storage section can be displayed on the display section as replay images of a scene that the user viewed in a recent past.

The user is likely to desire to store, more or less on a permanent basis, image data of a scene that is interesting for the user. Accordingly, according to an embodiment of the present invention, when the predetermined storage condition has been satisfied, relevant image data is extracted from the temporary storage section and stored by the storage process.

The storage process is a process of causing the storage section inside the imaging apparatus, for example, to store the extracted image data in a nonvolatile storage medium such as a hard disk drive (HDD), an optical disk, a magneto-optical disk, a magnetic disk, or a flash memory, or a process of causing the transmission section to transmit the extracted image data to the external device so that the extracted image data can be stored in an HDD or the like in the external device. In addition, the metadata is added to the image data to be stored, and the metadata will be useful when searching for the stored image data, for example.

According to an embodiment of the present invention, it is possible to store, temporarily, image data of scenes that the user views in his or her daily life, and it is also possible, when the predetermined storage condition has been satisfied, to perform the storage process of storing the image data together with the metadata.

Therefore, it is possible to extract, from the image data of such daily scenes obtained by constant imaging, the image data of the scene that has interested the user or the scene that the user desires to watch again later, and store the extracted image data properly to make the image data available for use.

BRIEF DESCRIPTION OF THE DRAWINGS

FIGS. 10A and 10B are diagrams illustrating a temporary storage section and a replay operation according to one embodiment of the present invention;

DETAILED DESCRIPTION OF THE PREFERRED EMBODIMENTS

Hereinafter, imaging apparatuses and an imaging method according to embodiments of the present invention will be described in the following order.
[1. Exemplary appearances of imaging apparatus]
[2. Exemplary structures of imaging apparatus]
[3. Exemplary photographed images]
[4. Replay operation]

[5. Exemplary manners for selecting image to be stored]
[6. Exemplary procedures]
[7. Imaging apparatus dedicated to replaying]
[8. Effects of embodiments]

1. Exemplary Appearances of Imaging Apparatus

Figure 1:
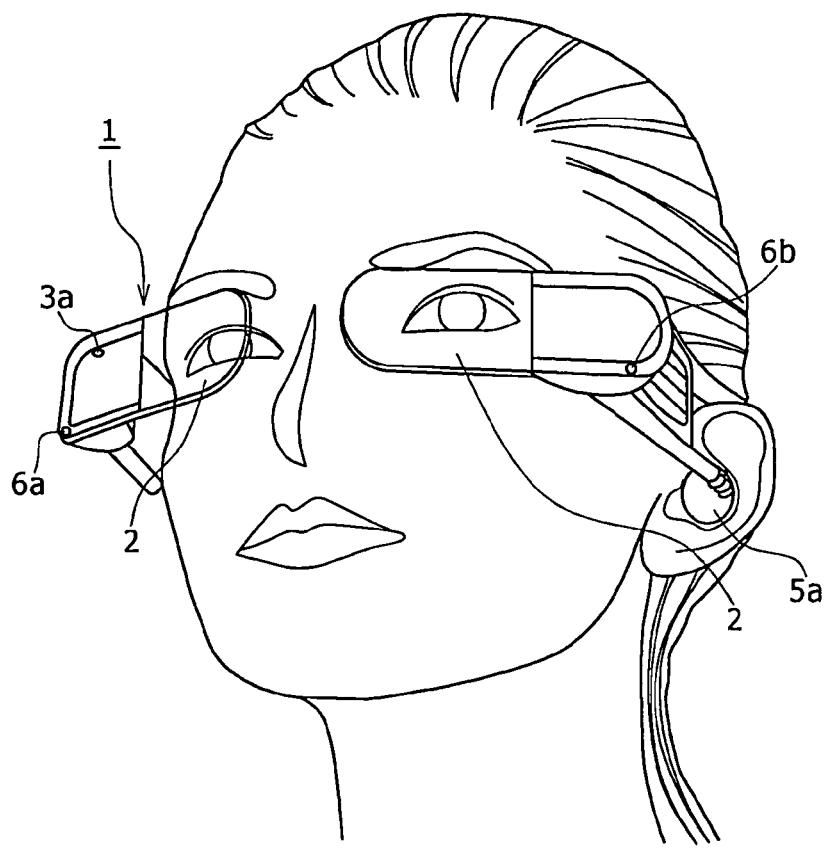
FIG. 1 is an illustration of an exemplary appearance of an imaging apparatus according to one embodiment of the present invention.

FIG. 1 shows an exemplary appearance of an imaging apparatus 1, which is a spectacle-shaped display camera, according to one embodiment of the present invention. The imaging apparatus 1 has a wearing unit having a frame structure that extends halfway around a head from both temporal regions to an occipital region, for example, and is worn by a user with the wearing unit placed over ears as illustrated in this figure.

The imaging apparatus 1 has a pair of display sections 2 designed for left and right eyes, and the display sections 2 are arranged in front of the eyes of the user (i.e., at positions where lenses of common spectacles would be located) when the imaging apparatus 1 is worn by the user in a manner as illustrated in FIG. 1. Liquid crystal panels, for example, are used for the display sections 2, and the display sections 2 are capable of entering a see-through state, i.e., a transparent or translucent state, as illustrated in this figure by transmissivity control. The capability of the display sections 2 to enter the see-through state allows the user to wear the imaging apparatus 1 at all times as he or she wears spectacles, with no interference occurring in his or her daily life.

In addition, the imaging apparatus 1 has a photographic lens 3*a* arranged to face forward so as to image a scene that is in a direction in which the user sees while the imaging apparatus 1 is worn by the user.

In addition, the imaging apparatus 1 has a pair of earphone speakers 5*a* that can be inserted into right and left earholes of the user when the imaging apparatus 1 is worn by the user. Note that only the left earphone speaker 5*a* is shown in the figure.

In addition, the imaging apparatus 1 has microphones 6*a* and 6*b* for collecting external sounds. The microphones 6*a* and 6*b* are arranged to the right of the right display section 2 and to the left of the left display section 2, respectively.

Note that FIG. 1 shows one example, and that various structures are possible for the user to wear the imaging apparatus 1. In general, a requirement for the wearing unit is that it be in the shape of spectacles or of a head-worn type. At least, a requirement for the present embodiment is that the display sections 2 be arranged in front of and close to the eyes of the user, and that the direction in which the photographic lens 3*a* photographs is a direction in which the eyes of the user are directed, i.e., in a forward direction. Also note that, instead of having the pair of display sections 2 provided for both eyes, the imaging apparatus 1 may have only one of the display sections 2 provided for one eye.

Also note that the imaging apparatus 1 need not have the left and right stereo speakers 5*a*, but may have only one of the earphone speakers 5*a* to be inserted into only one earhole. Also note that the number of microphones may be one. That is, the imaging apparatus 1 may have only one of the microphones 6*a* and 6*b*. Also note that the imaging apparatus 1 need not have any microphone or earphone speaker.

Also note that the imaging apparatus may have a lighting section that provides illumination in a direction of photographing by the photographic lens 3*a*. The lighting section is formed by a light emitting diode (LED), for example.

In the imaging apparatus 1 illustrated in FIG. 1, a component for imaging and the display-sections 2 for monitoring an image obtained by imaging are integrated in one unit. However, as with an imaging apparatus 1 as illustrated in FIG. 2, a case containing the display section may be provided separately from a case containing the component for imaging.

Figure 2:
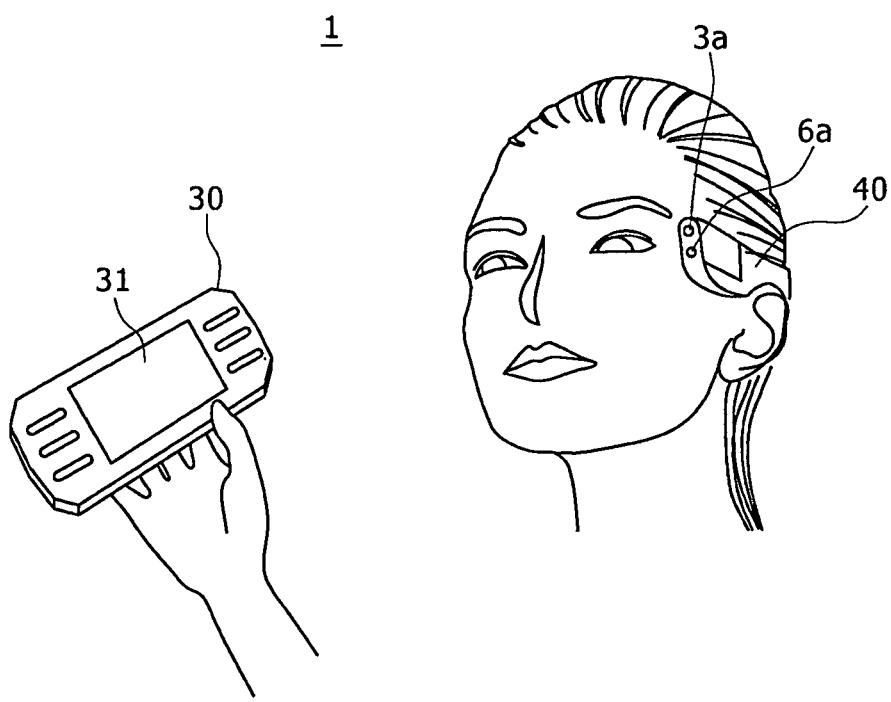
FIG. 2 is an illustration of an exemplary appearance of another imaging apparatus according to one embodiment of the present invention.

The imaging apparatus 1 as illustrated in FIG. 2 includes an imaging apparatus section 40 and a display apparatus section 30, which are separate from each other.

The imaging apparatus section 40 is worn on a head of the user via a predetermined wearing frame. The imaging apparatus section 40 has the photographic lens 3*a*, which is arranged to face forward so as to image a scene that is in the direction in which the user sees while the imaging apparatus section 40 is worn by the user. In addition, the imaging apparatus section 40 has the microphone 6*a* for collecting the external sounds.

In this case, as described below, the imaging apparatus section 40 contains a communication section for transmitting the image data obtained by imaging and so on to the display apparatus section 30, which is provided separately from the imaging apparatus section 40.

The display apparatus section 30 is, for example, a small and light device that the user is able to carry.

The display apparatus section 30 contains a communication section internally for performing data communication with the imaging apparatus section 40, and performs an operation of allowing the image data supplied from the imaging apparatus section 40 to be displayed on a display screen 31.

The user is able to use the imaging apparatus 1 in which the imaging apparatus section 40 and the display apparatus section 30 are separate from each other as described above.

Here, a portable display apparatus has been cited as the display apparatus section 30. However, the display apparatus section 30 may be a stationary display apparatus, a computer apparatus, a television receiver, a mobile phone, a personal digital assistant (PDA), or the like, for example. In short, in the case of the imaging apparatus 1 as illustrated in FIG. 2, which does not have a monitor display capability (and even in the case of the imaging apparatus 1 as illustrated in FIG. 1, which has the monitor display capability), the image data can be monitored with any external display apparatus.

Note that examples of external devices to which the image data obtained by imaging can be transmitted by the imaging apparatus 1 via its communication capability include, in addition to the various display devices as mentioned above, a video storage device, a computer apparatus, and a server apparatus. That is, it is conceivable that the photographed image data is stored in or delivered by such an external device.

Also note that the appearance of the imaging apparatus 1 is not limited to the examples of FIGS. 1 and 2, but that various types of variations are possible.

The above examples of the imaging apparatus 1 have the spectacle-shaped and head-worn wearing units, respectively. Note, however, that the wearing unit used for the user to wear the imaging apparatus may be of any type, such as a headphone type, a neckband type, a behind-the-ear type, or the like. Further, the imaging apparatus may be attached to common spectacles, visor, headphone, or the like via a fixing device, such as a clip, so that the imaging apparatus can be worn by the user. Also note that it is not necessary that the imaging apparatus be worn on the head of the user.

2. Exemplary Structures of Imaging Apparatus

Here, three exemplary structures of the imaging apparatus 1 according to embodiments of the present invention will be described with reference to FIGS. 3, 4, and 5. Exemplary structures illustrated in FIGS. 3 and 4 correspond to the case where the imaging apparatus 1 is the spectacle-shaped display camera as illustrated in FIG. 1, which has both an imaging function and a display function. Meanwhile, an exemplary structure illustrated in FIG. 5 corresponds to the case where the imaging apparatus section 40 and the display apparatus section 30 are provided separately as illustrated in FIG. 2.

First, the exemplary structure of FIG. 3 will now be described below.

A system controller 10 is formed by a microcomputer that includes a central processing unit (CPU), a read only memory (ROM), a random access memory (RAM), a nonvolatile memory section, and an interface section, for example, and controls an overall operation of the imaging apparatus 1. The system controller 10 controls each part of the imaging apparatus 1 to perform a predetermined operation based on a program held in the internal ROM or the like.

The imaging apparatus 1 includes, as units for imaging the scene that is in the direction in which the user sees, an imaging section 3, an imaging control section 11, and an imaging signal processing section 15.

The imaging section 3 includes: a lens system formed by the photographic lens 3a illustrated in FIG. 1, a diaphragm, a zoom lens, a focus lens, and the like; a driving system for allowing the lens system to perform a focusing operation, a zoom operation, and the like; and a solid-state imaging device array for detecting light for imaging obtained by the lens system, and subjecting the detected light to photoelectric conversion to generate an imaging signal. The solid-state imaging device array is, for example, a charge coupled device (CCD) sensor array or a complementary metal oxide semiconductor (CMOS) sensor array.

The imaging signal processing section 15 includes a sample-hold/automatic gain control (AGC) circuit for subjecting the signal obtained by the solid-state imaging device in the imaging section 3 to gain control and waveform shaping, and a video A/D converter, and obtains an imaging signal in digital form.

In addition, the imaging signal processing section 15 performs white balancing processing, brightness processing, color signal processing, blur correction processing, and the like on the imaging signal. Further, the imaging signal processing section 15 is also capable of performing processes such as: brightness level control, color correction, contrast control, and sharpness (edge enhancement) control for the imaging signal; generation of a magnified image in which a part of the imaging signal is magnified; generation of a reduced image in which a part of the imaging signal is reduced; application of image effects such as mosaicing, brightness reversal, soft focus, highlighting of a part of the image, and varying of the overall color atmosphere of the image; generation of a character image or a conceptual image; and combination of a generated image with the photographed image. In short, the imaging signal processing section 15 is capable of performing various processes on a digital video signal as the imaging signal.

Based on an instruction issued from the system controller 10, the imaging control section 11 controls an imaging operation performed by the imaging section 3 and the imaging signal processing section 15. For example, the imaging control section 11 controls activation and deactivation of the operations of the imaging section 3 and the imaging signal processing section 15. In addition, the imaging control section 11 exercises control (motor control) for allowing the imaging section 3 to perform an operation such as autofocusing, automatic exposure adjustment, aperture adjustment, zooming, or focus change.

The imaging control section 11 includes a timing generator, and uses a timing signal generated by the timing generator to control signal processing operations performed by the solid-state imaging device, and the sample-hold/AGC circuit and the video A/D converter in the imaging signal processing section 15. Moreover, such timing control enables adjustment of an imaging frame rate.

In addition, the imaging control section 11 controls imaging sensitivity and signal processing in the solid-state imaging device and the imaging signal processing section 15. For example, as control of the imaging sensitivity, the imaging control section 11 is capable of performing the gain control on the signal read from the solid-state imaging device, and black level setting, control of various coefficients in processing the imaging signal in digital form, control of a correction value in the blur correction processing, and the like. Regarding the control of the imaging sensitivity, overall sensitivity adjustment with no regard to any particular wavelength range, and sensitivity adjustment of adjusting imaging sensitivity of a particular wavelength range such as an infrared range or an ultraviolet range (for example, imaging that involves cutting off the particular wavelength range) are possible, for example. Sensitivity adjustment in accordance with the wavelength is achieved by insertion of a wavelength filter in a photographic lens system or a wavelength filter operation process performed on the imaging signal. In these cases, the imaging control section 11 achieves the sensitivity control by controlling the insertion of the wavelength filter, specification of a filter operation coefficient, or the like.

Further, based on an instruction issued from the system controller 10, the imaging control section 11 controls the above-described image processing operation performed by the imaging signal processing section 15.

A temporary storage section 23 is a storage section that uses a solid-state memory, such as a dynamic random access memory (D-RAM) or a static random access memory (S-RAM), as a storage medium. Note, however, that the temporary storage section 23 may be constructed as a unit for recording and reproducing data onto or from a storage medium such as a flash memory, an optical disk, a magnetic disk, or a memory card containing the flash memory. Further, the temporary storage section 23 may be formed by an HDD.

The temporary storage section 23 stores the image data constantly obtained by imaging performed by the above-described imaging system (hereinafter, the imaging section 3, the imaging signal processing section 15, and the imaging control section 11 will be referred to collectively as the "imaging system"). That is, when the image data has been supplied, the temporary storage section 23 performs a predetermined encoding process for storage on the image data and stores the encoded image data in the storage medium. In addition, under control of the system controller 10, the temporary storage section 23 is capable of reading the stored image data from the storage medium, and decoding and outputting the image data.

FIG. 10A is a schematic diagram of a storage area of the memory, such as the D-RAM, in the temporary storage section 23. The storage area, which extends from a top address AdST to an end address AdED, is used in a ring memory manner. Specifically, the image data is written to an address indicated by a write address pointer W-Ad, which moves from the top address AdST toward the end address AdED and, when it has reached the end address AdED, returns to the top address AdST. In such a manner, the image data is recorded on the storage area continuously.

Therefore, image data obtained in a period from a predetermined time ago up to the present is stored temporarily in the temporary storage section 23. Naturally, how long the image data is stored therein depends on the capacity of the temporary storage section 23 and a rate (e.g., a frame rate, a data amount per frame, etc.) of the image data.

The frame rate at which the imaging system takes a video to be stored in the temporary storage section 23 may be set at any value. The image data obtained by imaging performed by the imaging system and stored in the temporary storage section 23 may have either a normal frame rate (e.g., 30 frames per second, for example) or a higher frame rate. It is also possible to extract several frames from the photographed image data in each second, for example, and allow the temporary storage section 23 to store resultant pseudo-moving image data. Moreover, it is also possible to extract one frame every one to several seconds, for example, and allow the temporary storage section 23 to store image data in the form of still images obtained at intervals of one to several seconds.

The imaging signal (i.e., the image data obtained by imaging) obtained by imaging by the imaging section 3 and processing by the imaging signal processing section 15 is supplied to an image input/output control section 27.

Under control of the system controller 10, the image input/output control section 27 controls transfer of the image data. Specifically, the image input/output control section 27 controls the transfer of the image data among the imaging system (i.e., the imaging signal processing section 15), the temporary storage section 23, a display image processing section 12, and a storage section 25.

In the imaging apparatus 1 according to the present embodiment, the imaging system basically performs the imaging operation constantly, and the image data obtained by imaging is transferred to the temporary storage section 23 via the image input/output control section 27 and temporarily stored in the temporary storage section 23. Thus, the image data constantly obtained by imaging is constantly recorded in the temporary storage section 23 in the above-described manner, so that image data obtained by imaging in a period from a certain time before up to the present is stored therein constantly.

Under control of the system controller 10, the image input/output control section 27 is also capable of supplying the imaging signal (i.e., the image data) processed by the imaging signal processing section 15 to the display image processing section 12.

In addition, the image input/output control section 27 is also capable of supplying image data read from the storage section 25, for example, to the display image processing section 12.

Further, under control of the system controller 10, the image input/output control section 27 is capable of supplying image data read from the temporary storage section 23 (i.e., some of the image data temporarily stored in the temporary storage section 23) to the display image processing section 12 or the storage section 25.

The storage section 25 is a unit for recording and reproducing data onto or from a predetermined storage medium (e.g., a nonvolatile storage medium). The storage section 25 is formed by a hard disk drive (HDD), for example. Needless to say, as the nonvolatile storage medium, various types of storage media are adoptable such as: a solid-state memory such as a flash memory, a memory card containing a fixed memory, an optical disk, a magneto-optical disk, and a hologram memory. A requirement for the storage section 25 is to be capable of recording and reproducing the data in accordance with the adopted storage medium.

Unlike the above-described temporary storage section 23, the storage section 25 is provided for storing the image data not temporarily but semi-permanently.

In particular, in the case where some of the image data temporarily stored in the temporary storage section 23 has been selected as a subject of a storage process, the selected image data is read from the temporary storage section 23 and supplied to the storage section 25 via the image input/output control section 27. Under control of the system controller 10, the storage section 25 encodes the supplied image data so that it can be recorded on the storage medium, and records the encoded image data on the storage medium.

That is, the storage section 25 performs a process of, when a predetermined condition for storage (hereinafter referred to as a "storage condition") has been satisfied, storing, in the HDD, image data that has been determined to be an object to be stored among the image data temporarily stored in the temporary storage section 23.

When controlling the storage section 25 to perform the above process of storing the image data, the system controller 10 generates metadata and controls the storage section 25 to record the generated metadata together with the image data.

In addition, under control of the system controller 10, the storage section 25 is capable of reproducing the recorded image data. The reproduced image data is supplied to the display image processing section 12 via the image input/output control section 27.

Although not shown in the figures, the reproduced image data may also be output to an external device via a predetermined interface section so as to be displayed by an external monitoring device or stored in an external storage device, for example.

The imaging apparatus 1 includes, as units for presenting a display to the user, the display section 2, the display image processing section 12, a display driving section 13, and a display control section 14.

Under control of the system controller 10, the image data read from the temporary storage section 23 (i.e., the image data obtained by imaging in the recent past), the image data obtained by imaging by the imaging section 3 and processed by the imaging signal processing section 15 (i.e., the image data that is being currently obtained by imaging), or the image data read from the storage section 25 (i.e., the stored image data) is supplied to the display image processing section 12 via the image input/output control section 27.

The display image processing section 12 performs signal processing (e.g., the brightness level control, the color correction, the contrast control, the sharpness (edge enhancement) control, etc., for example) for displaying the supplied image data on the display section 2, a split screen process, synthesis of the character image, or the like.

The display driving section 13 is formed by a pixel driving circuit for allowing an image signal supplied from the display image processing section 12 to be displayed on the display section (e.g., a liquid crystal display) 2. That is, the display driving section 13 applies driving signals based on a video signal to pixels arranged in a matrix in the display section 2 with specified horizontal/vertical driving timing for displaying. In addition, the display driving section 13 is capable of controlling transmissivity of each of the pixels in the display section 2 to allow the pixel to enter the see-through state.

Based on an instruction issued from the system controller 10, the display control section 14 controls a processing operation of the display image processing section 12 and an operation of the display driving section 13. Specifically, the display control section 14 controls the display image processing section 12 to perform the aforementioned various processes.

Also, the display control section 14 controls the display driving section 13 to switch between the see-through state and an image displaying state.

The imaging apparatus 1 further includes an audio input section 6, an audio signal processing section 16, and an audio output section 5.

The audio input section 6 includes the microphones 6a and 6b illustrated in FIG. 1, a microphone amplifier section for amplifying audio signals obtained by the microphones 6a and 6b, and an A/D converter, and outputs audio data.

The audio data obtained by the audio input section 6 is supplied to an audio input/output control section 28.

Under control of the system controller 10, the audio input/output control section 28 controls transfer of the audio data. Specifically, the audio input/output control section 28 controls transfer of the audio data among the audio input section 6, the audio signal processing section 16, the temporary storage section 23, and the storage section 25.

Basically, the audio input/output control section 28 constantly supplies the audio data obtained by the audio input section 6 to the temporary storage section 23. As a result, the temporary storage section 23 constantly stores the audio data obtained by the collecting of sound by the microphones 6a and 6b together with the image data obtained by imaging performed by the imaging system.

In addition, the audio input/output control section 28 performs a process of supplying the audio data obtained by the audio input section 6 to the audio signal processing section 16.

Further, in the case where the temporary storage section 23 reads out data, the audio input/output control section 28 performs a process of supplying audio data read out by the temporary storage section 23 to the audio signal processing section 16 or the storage section 25.

Still further, in the case where the storage section 25 reads out data, the audio input/output control section 28 performs a process of supplying audio data read out by the storage section 25 to the audio signal processing section 16.

The audio signal processing section 16 is formed by a digital signal processor, a D/A converter, and the like, for example. Under control of the system controller 10, the audio signal processing section 16 performs a process such as volume control, tone control, or application of a sound effect on the audio data supplied via the audio input/output control section 28. Then, the audio signal processing section 16 converts the processed audio data into an analog signal, and supplies the analog signal to the audio output section 5. Note that the audio signal processing section 16 is not limited to a unit that performs digital signal processing, but may be a unit that performs signal processing using an analog amplifier, an analog filter, or the like.

The audio output section 5 includes the pair of earphone speakers 5a illustrated in FIG. 1 and an amplifier circuit for the earphone speakers 5a.

The audio input section 6, the audio signal processing section 16, and the audio output section 5 enable the user to listen to an external sound, audio reproduced by the temporary storage section 23, and audio reproduced by the storage section 25.

Note that the audio output section 5 may be formed by a so-called bone conduction speaker.

The imaging apparatus 1 is provided with an operation input section 20 for user operation.

The operation input section 20 may include an operation unit such as a key, a dial, or the like, and be configured to detect a user operation such as a key operation. Alternatively, the operation input section 20 may be configured to detect a deliberate behavior of the user.

In the case where the operation input section 20 is provided with the operation unit, the operation input section 20 may be provided with an operation unit for a replay operation, which will be described later, an operation unit for an operation (e.g., the zoom operation, signal processing, etc.) performed by the imaging system, and the like, for example.

In the case where the operation input section 20 is configured to detect a user behavior, the operation input section 20 may be provided with an acceleration sensor, an angular velocity sensor, a vibration sensor, a pressure sensor, or the like.

For example, the user's act of tapping the imaging apparatus 1 from the side may be detected with the acceleration sensor, the vibration sensor, or the like. Thus, the system controller 10 may determine that a user operation has occurred when lateral acceleration has exceeded a predetermined value, for example. For example, when the user has tapped the imaging apparatus 1 once, the system controller 10 may determine that the user has performed a replay start operation, whereas when the user has tapped the imaging apparatus 1 twice, the system controller 10 may determine that the user has performed a replay termination operation. Moreover, the acceleration sensor, the angular velocity sensor, or the like may be used to detect whether the user has tapped a side (which corresponds to a sidepiece of spectacles) of the imaging apparatus 1 from the right side or from the left side, and the system controller 10 may regard each of these acts of the user as a predetermined operation.

Further, the user's act of turning or shaking his or her head may be detected with the acceleration sensor, the angular velocity sensor, or the like. The system controller 10 may regard each of these acts of the user as a user operation.

Still further, the pressure sensor may be provided on each of left and right sides (which correspond to the sidepieces of the spectacles) of the imaging apparatus 1, for example. Then, the system controller 10 may determine that the user has performed an operation for telephoto zooming when the user has pushed the right side of the imaging apparatus 1, and determine that the user has performed an operation for wide-angle zooming when the user has pushed the left side of the imaging apparatus 1.

The operation input section 20, which acquires information by functioning as the operation unit, the acceleration sensor, the angular velocity sensor, the vibration sensor, the pressure sensor, or the like as described above, supplies the acquired information to the system controller 10, and the system controller 10 detects the user operation based on the supplied information.

Next, the biological sensor 21 will now be described below. The system controller 10 may recognize information detected by the biological sensor 21 as an operation input by the user. One example of deliberate behaviors of the user is a motion of the eyes (e.g., a change in the direction in which the eyes of the user are directed, winking, etc.). A visual sensor, which will be described later, may be used to detect winking. For example, the system controller 10 may regard the user's act of winking three times as a specific operation input.

A power operation unit may be provided for turning the power of the imaging apparatus 1 on and off. Alternatively, the system controller 10 may automatically turn the power on when the biological sensor 21 has detected that the user has put on the imaging apparatus 1, and automatically turn the power off when the user has taken off the imaging apparatus 1.

The biological sensor 21 detects biological information concerning the user. Examples of the biological information include a pulse rate, a heart rate, electrocardiogram information, electromyographic information, breathing information (e.g., a rate of breathing, a depth of breathing, the amount of ventilation, etc.), perspiration, galvanic skin response (GSR), blood pressure, a saturation oxygen concentration in the blood, a skin surface temperature, brain waves (e.g., information of alpha waves, beta waves, theta waves, and delta waves), a blood flow change, and the state of the eyes.

In order to detect the galvanic skin response, a body temperature, the skin surface temperature, an electrocardiographic response, the electromyographic information, heart beats, a pulse, a blood flow, the blood pressure, the brain waves, the perspiration, or the like, a sensor that is attached to an inside of the wearing frame as illustrated in FIG. 1, for example, so as to be in contact with the temporal region or the occipital region of the user or a sensor that is separate from the wearing frame and attached to another body part of the user may be used.

Further, an imaging section for imaging the skin of the user may be used. This imaging section is a sensor capable of detecting a change in skin color, for example.

A visual sensor including an imaging section that is arranged near the display section 2, for example, to photograph the eye of the user may be used as a sensor for detecting vision of the user. In this case, an image of the eye of the user taken by this imaging section may be subjected to image analysis to detect the direction in which the eye is directed, a focal distance, the degree of dilation of a pupil of the eye, a fundus pattern, opening and closing of an eyelid, and the like. Further, a lighting section that is arranged near the display section 2 to emit light to the eye of the user and a light-receiving section for receiving the light reflected from the eye may be used. In this case, it is possible to detect the thickness of a crystalline lens of the user based on the received reflected light, for example.

The biological sensor 21 supplies information of such detection by such a sensor to the system controller 10.

The acceleration sensor, the angular velocity sensor, the vibration sensor, and so on have been cited as the sensors that may be included in the operation input section 20. Such sensors are capable of detecting a motion of a body of the user, a motion of the head, the center of gravity, the rhythm of walking/running, or the like. In the above description of the operation input section 20, the deliberate behaviors (i.e., "operations" by the user) have been mentioned as a motion to be detected by such sensors. However, it may be so arranged that a behavior which the user does not intend as an "operation", such as the motion of the body of the user, the motion of the head, the center of gravity, or the rhythm of walking/running, is detected by the acceleration sensor or the like, and that such a behavior is treated as one piece of biological information.

The imaging apparatus 1 further includes an audio analysis section 24.

The audio analysis section 24 analyzes the audio data of the external sound obtained by the audio input section 6. For example, the audio analysis section 24 performs frequency analysis, amplitude level evaluation, voiceprint analysis, or the like, and supplies resultant analysis information to the system controller 10.

In the imaging apparatus 1, the imaging system constantly performs imaging, and the image data obtained by imaging is temporarily stored in the temporary storage section 23 in the ring memory manner, and when the predetermined storage condition has been satisfied, the system controller 10 extracts, from the image data temporarily stored in the temporary storage section 23 at the time, image data to be stored and transfers the extracted image data to the storage section 25 so as to be recorded therein on a permanent basis.

Here, the image data to be stored on a permanent basis in the storage section 25 is, among the images obtained by constant imaging, an image that the system controller 10 has determined to be an image of a scene that has some meaning for the user, such as an image of a scene that has interested the user, an image of a scene at a time when a change has occurred in the user's feelings, an image of a scene that is likely to remain in the user's memory, or an image of a scene that the user is likely to desire to see again later.

The storage condition is satisfied when the system controller 10 infers that such an image is currently stored in the temporary storage section 23. For example, the system controller 10 determines that the storage condition has been satisfied in the following cases.

First, an image that the user has caused to be replayed and an image concerning which the user has issued an instruction related to an operation of the imaging system, such as zoom photographing, can be regarded as an image (of a scene) that has interested the user. Therefore, the system controller 10 may determine that the storage condition has been satisfied when replaying has been performed in response to the user operation or when an operation concerning the imaging system, such as zooming, has been performed.

When the user has become interested in a scene within his or her field of vision or when a change has occurred in his or her feelings, corresponding biological information concerning the user is obtained. Therefore, the system controller 10 may determine that the storage condition has been satisfied when a predetermined detection value has been obtained as the biological information. For example, the system controller 10 may determine that the storage condition has been satisfied when a predetermined situation has been detected by the biological sensor 21. Examples of such predetermined situations include: a situation in which the heart rate has exceeded its normal range; a situation in which the perspiration, the blood pressure, or the like has deviated from its normal state; and a situation in which a line of sight of the user has moved abruptly.

Further, in the present embodiment, the external sound is analyzed by the audio analysis section 24. Thus, the system controller 10 may determine that the storage condition has been satisfied when a loud sound has occurred suddenly or when a situation in which loud cheers or the like are being shouted or voice of a specific person has been detected.

As described above, the system controller 10 performs a control process in accordance with the user operation inputted from the operation input section 20, and a process of determining that the storage condition has been satisfied based on the information detected by the biological sensor 21 or the analysis information obtained by the audio analysis section 24. When the storage condition has been satisfied, the system controller 10 performs, as the storage process, a process of controlling the storage section 25 to record the image data extracted from the temporary storage section 23 on the storage medium. When performing the storage process, the system controller 10 generates the metadata in accordance with the storage condition, and adds the generated metadata to the image data so that the generated metadata will be recorded together with the image data.

Next, an exemplary structure of FIG. 4 will now be described below. Note that, in FIG. 4, components that have their counterparts in FIG. 3 are assigned the same reference numerals as those of their counterparts in FIG. 3, and descriptions thereof will be omitted. The structure of FIG. 4 is the same as the structure of FIG. 3 except that a communication section 26 is included in place of the storage section 25.

The communication section 26 transmits and receives data to and from the external device. Examples of such external devices include a variety of electronic devices such as a computer device, a personal digital assistant (PDA), a mobile phone, a monitoring device, a video device, and a storage device. In particular, any device that has a capability to store the image data transmitted from the communication section 26 in an HDD or other storage media may be used as such an external device.

Other examples of the external device with which the communication section 26 is capable of communicating include a terminal device, a server device, and the like connected to a network such as the Internet.

The communication section 26 may be configured to perform network communication via short-range wireless communication for a network access point, for example, in accordance with a system such as a wireless LAN, Bluetooth, or the like. Alternatively, the communication section 26 may perform wireless communication directly with the external device having a corresponding communication capability.

The image data (and the audio data) read from the temporary storage section 23 is supplied to the communication section 26 via the image input/output control section 27 (and the audio input/output control section 28). In addition, the metadata is supplied from the system controller 10 to the communication section 26.

Under control of the system controller 10, the communication section 26 adds the metadata to the supplied image data (and the supplied audio data), encodes and modulates resultant data for transmission, and transmits resultant data to the external device.

Figure 3:
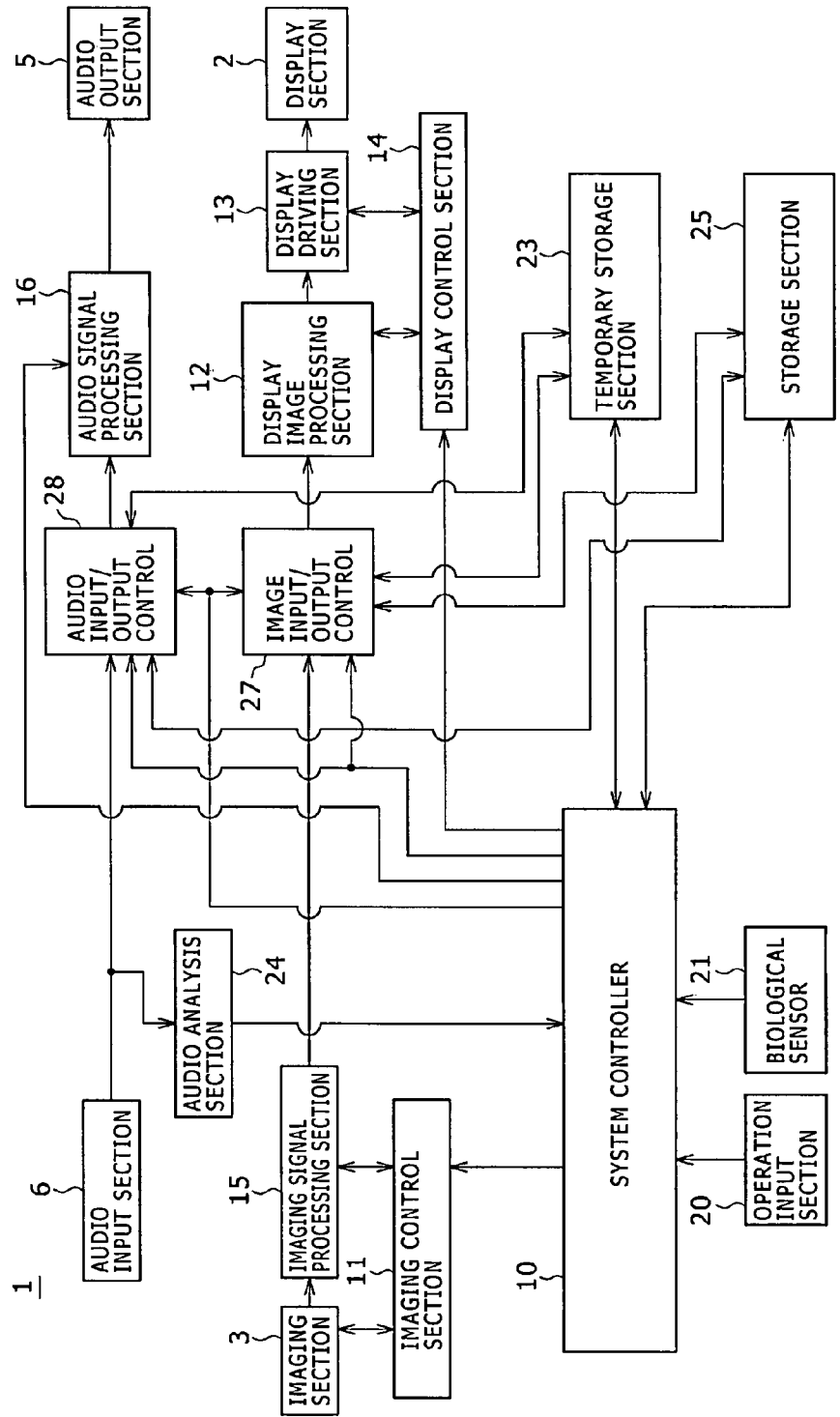
FIG. 3 is a block diagram of an imaging apparatus according to one embodiment of the present invention.

In the case of the exemplary structure of FIG. 3, the system controller 10 performs, as the storage process for storing the image temporarily stored in the temporary storage section 23 on a permanent basis, the process of controlling the storage section 25 to record the image therein. In contrast, in the case of the structure of FIG. 4, the system controller 10 performs, as the storage process for storing the image temporarily stored in the temporary storage section 23 on a permanent basis, the process of controlling the communication section 26 to transmit the image data to the external device.

Figure 4:
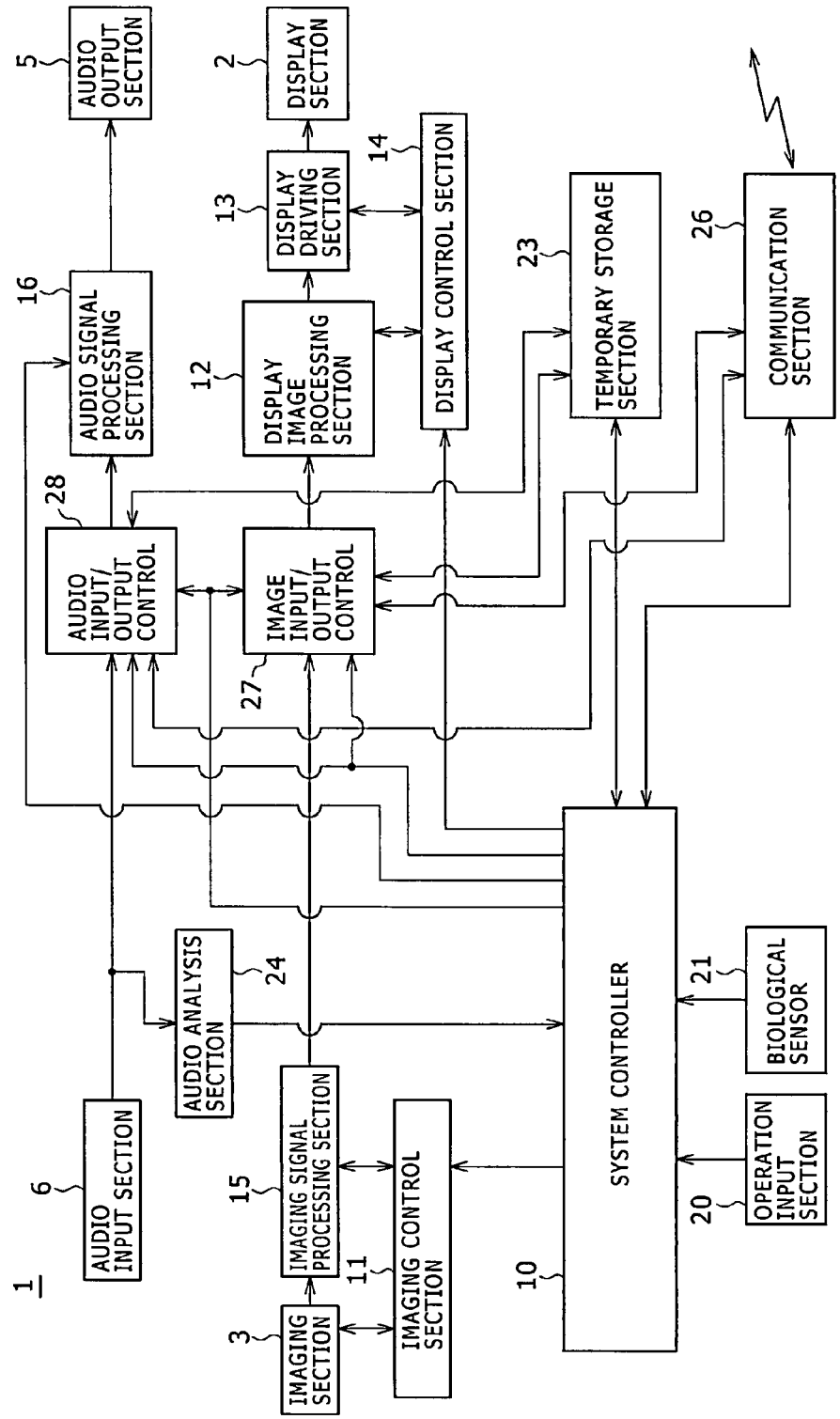
FIG. 4 is a block diagram of another imaging apparatus according to one embodiment of the present invention.

That is, with the exemplary structure of FIG. 4, the imaging apparatus 1 does not have a capability to store data on a permanent basis within itself. The exemplary structure of FIG. 4 depends on the assumption that the image data is stored in the external device.

The system controller 10 performs the control process in accordance with the user operation inputted from the operation input section 20, and the process of determining that the storage condition has been satisfied based on the information detected by the biological sensor 21 or the analysis information obtained by the audio analysis section 24. When the storage condition has been satisfied, the system controller 10 performs, as the storage process, a process of controlling the communication section 26 to transmit the image data extracted from the temporary storage section 23 (and the metadata) to the external device.

Figure 5:
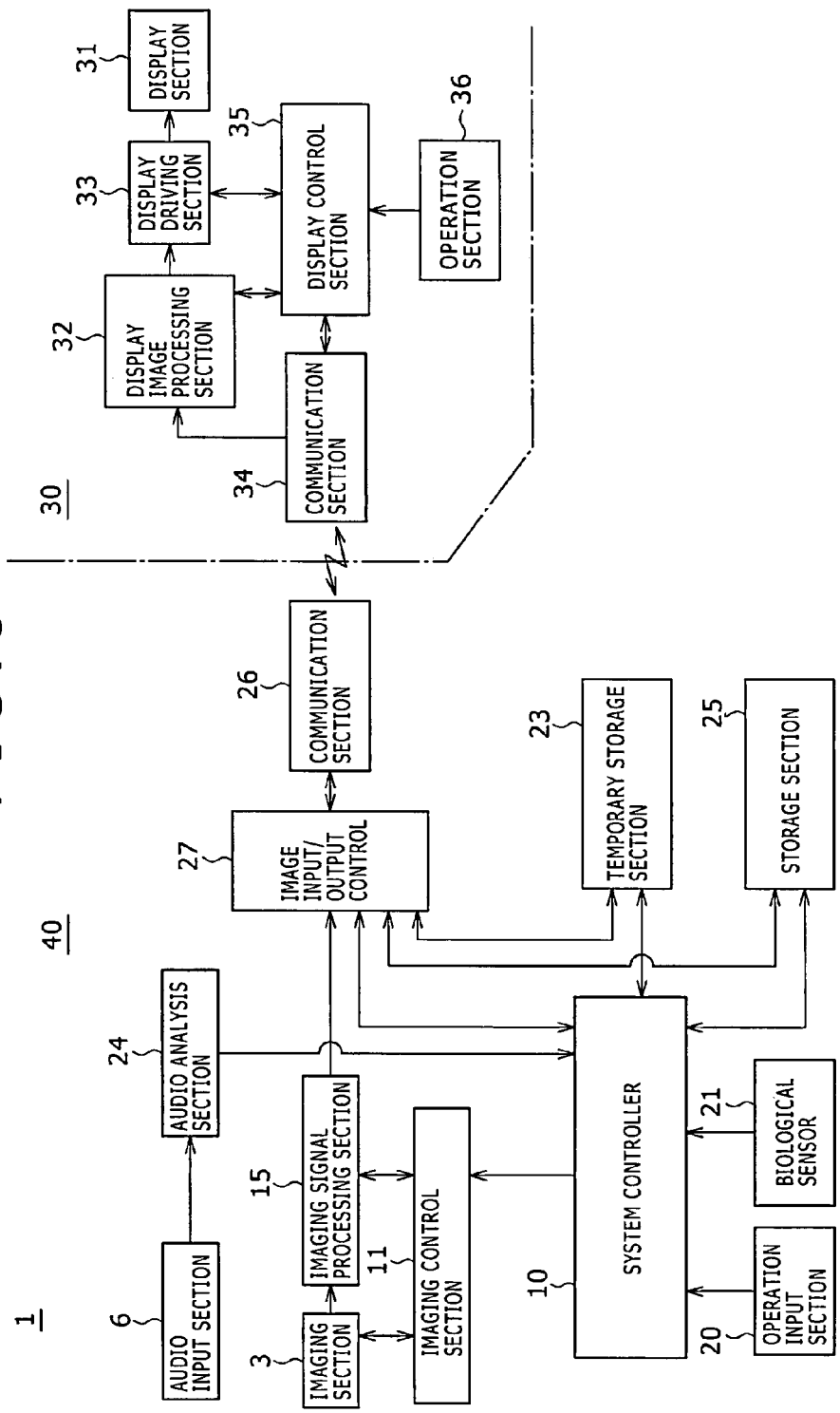
FIG. 5 is a block diagram of yet another imaging apparatus according to one embodiment of the present invention.

Next, FIG. 5 illustrates an exemplary structure of the imaging apparatus 1 in which the imaging apparatus section 40 and the display apparatus section 30 are provided separately as illustrated in FIG. 2.

In the case of this structure, the imaging apparatus section 40 includes the system controller 10, the imaging system (i.e., the imaging section 3, the imaging signal processing section 15, and the imaging control section 11), the temporary storage section 23, the storage section 25, the operation input section 20, the biological sensor 21, the image input/output control section 27, the audio input section 6, and the audio analysis section 24.

However, the imaging apparatus section 40 does not include the audio input/output control section 28, the audio signal processing section 16, or the audio output section 5. Thus, a signal of the external sound obtained by the audio input section 6 is used only in a process performed by the audio analysis section 24, i.e., determination concerning the storage condition. Therefore, in this exemplary structure, the audio data is neither temporarily stored in the temporary storage section 23 nor stored in the storage section 25.

The image input/output control section 27 performs a process of transferring the image data constantly obtained by the imaging system to the temporary storage section 23. The image input/output control section 27 also performs a process of transferring the image data read from the temporary storage section 23 to the communication section 26 or the storage section 25. The image input/output control section 27 also performs a process of transferring the image data read from the storage section 25 to the communication section 26.

The communication section 26 performs an encoding process on the supplied image data for transmission to the display apparatus section 30. Then, the communication section 26 transmits the encoded image data to the display apparatus section 30.

The display apparatus section 30 includes a communication section 34, a display section 31, a display image processing section 32, a display driving section 33, a display control section 35, and an operation section 36.

The communication section 34 performs data communication with the communication section 26 in the imaging apparatus section 40. The communication section 34 receives the image data transmitted from the imaging apparatus section 40, and performs a decoding process on the received image data.

The image data decoded by the communication section 34 is supplied to the display image processing section 32. The display image processing section 32 performs signal processing for displaying the image data, the split screen process, synthesis of the character image, or the like.

The display driving section 33 is formed by a pixel driving circuit for allowing an image signal supplied from the display image processing section 32 to be displayed on the display section (e.g., a liquid crystal display) 31. That is, the display driving section 33 applies driving signals based on a video signal to pixels arranged in a matrix in the display section 31 with specified horizontal/vertical driving timing for displaying.

The display control section 35 controls a processing operation of the display image processing section 32 and an operation of the display driving section 33. For example, in accordance with a user operation inputted from the operation section 36, the display control section 35 controls activation and deactivation of a display operation, switching of the form of an area on a screen, or the like.

In the case where instruction information is transmitted from the system controller 10 via communication between the communication sections 26 and 34, the display control section 35 may control the activation and deactivation of the display operation, switching of the form of the area on the screen, or the like in accordance with the instruction information transmitted from the system controller 10.

While the exemplary structures of the imaging apparatus 1 have been described above with reference to FIGS. 3, 4, and 5, various other structures of the imaging apparatus 1 are possible.

For example, the structures of FIGS. 3 and 4 may be modified so as not to include a system for recording or outputting the audio data (i.e., the audio input/output control section 28, the audio signal processing section 16, and/or the audio output section 5) as is the case with the structure of FIG. 5. Conversely, the structure of FIG. 5 may be modified so as to additionally include the system for recording or outputting the audio data.

The imaging apparatus need not include the audio analysis section 24. The imaging apparatus need not include the biological sensor 21.

The structure of FIG. 5 may be modified so as to include the communication section 26 for transmitting the image data to be stored to the external device in place of the storage section 25.

The imaging apparatus may include both the storage section 25 and the communication section 26.

3. Exemplary Photographed Images

Here, with reference to FIGS. 6A to 9B, examples of the image data that are obtained by imaging performed by the imaging system and temporarily stored in the temporary storage section 23 will now be described below.

Figure 6A:
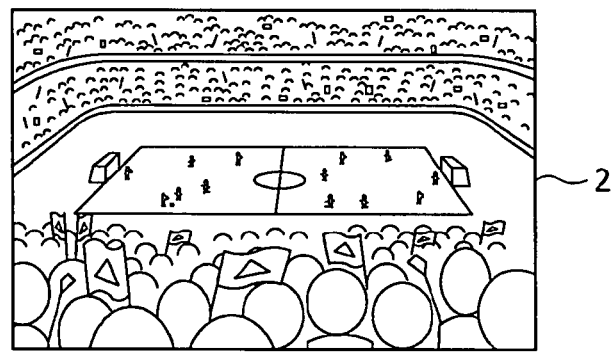
FIGS. 6A to 6C are illustrations for describing a see-through state, an image obtained by regular imaging, a telephoto image, respectively, according to one embodiment of the present invention.

However, FIG. 6A illustrates not an image obtained by imaging but an example of a scene that the user sees when the entire screen of the display section 2 as illustrated in FIG. 1 is in the see-through state. At this time, the display section 2 is in a state of being simply a transparent plate, and the user is viewing the scene within his or her field of vision through the transparent display section 2.

It is assumed that when the imaging section 3 photographs in a regular manner, an image equivalent to a scene that the user would see if the display section 2 were in the see-through state is obtained by imaging.

Figure 6B:
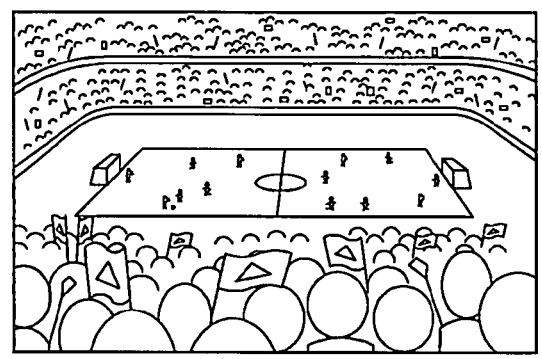

FIG. 6B illustrates an example of image data that is obtained when the imaging system photographs in the regular manner. This image data represents a scene that is nearly the same as the scene that the user would see if the display section 2 were in the see-through state. While the imaging system is imaging in the regular manner, images representing scenes that are approximately equivalent to scenes that the user would regularly see are obtained by imaging as described above, and image data of such images are sequentially stored in the temporary storage section 23.

Figure 6C:
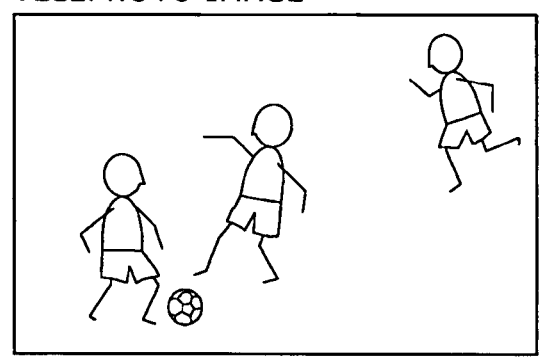

FIG. 6C illustrates an example of an image obtained by imaging when the system controller 10 has instructed the imaging control section 11 to control the imaging section 3 to take a telephoto in accordance with the user operation via the operation input section 20. Taking a telephoto allows image data of such a telephoto image to be obtained so that the image data of the telephoto image can be stored in the temporary storage section 23.

Note that although the example of telephotography has been described above, the imaging section 3 may be caused to perform wide-angle zooming to obtain image data of a wide-angle image of a scene nearby.

Acquisition by the imaging system of the telephoto/wide-angle images is achieved by drive control of the zoom lens in the imaging section 3 as well as by signal processing in the imaging signal processing section 15.

Although not shown in the figures, the system controller 10 may instruct the imaging section 3 to perform adjustment of a focal point instead of the so-called zoom operation to take an image of a scene nearby or a distant scene so that image data thereof can be stored in the temporary storage section 23.

Figure 7A:
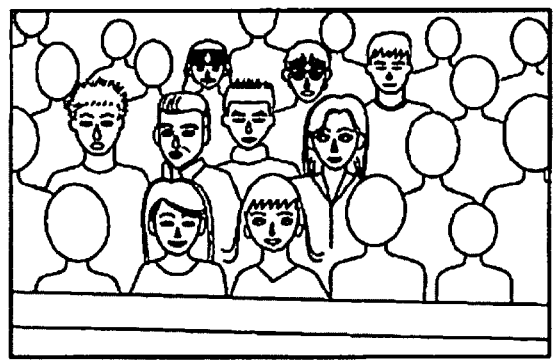
FIGS. 7A and 7B are illustrations for describing a magnified image according to one embodiment of the present invention.
Figure 7B:
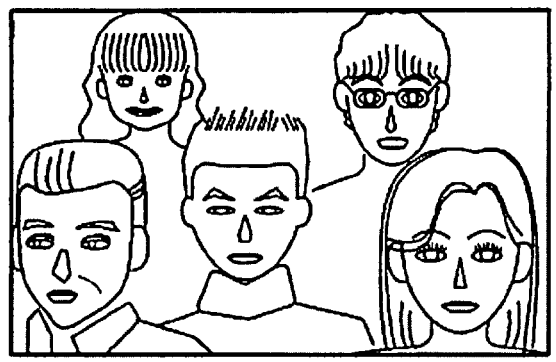

FIG. 7A illustrates an example of an image obtained by regular imaging, and FIG. 7B illustrates an example of a magnified image.

In accordance with the user operation, for example, the system controller 10 may instruct the imaging signal processing section 15 to perform a magnification process on the image obtained from the imaging section 3 to obtain image data of the magnified image as illustrated in FIG. 7B, and store the image data of the magnified image in the temporary storage section 23. Although not shown in the figures, the system controller 10 is also capable of instructing the imaging signal processing section 15 to perform a reduction process on the image, and storing a resultant reduced image in the temporary storage section 23.

Figure 8A:
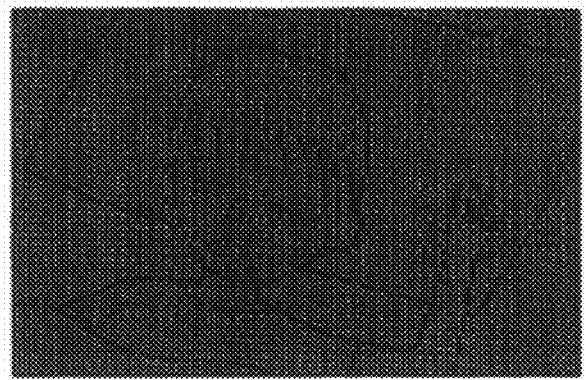
FIGS. 8A and 8B are illustrations for describing an image photographed with increased infrared sensitivity according to one embodiment of the present invention.

FIG. 8A illustrates an image obtained by regular imaging when the user is in a dark room where a child is sleeping, for example. Because the user is in the dark room, this image obtained by regular imaging does not show the child and so on clearly.

Figure 8B:
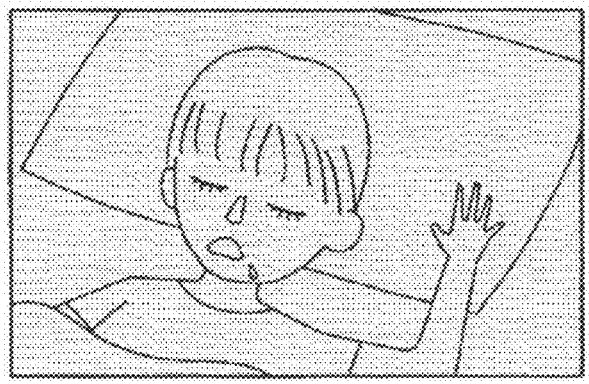

In this case, the system controller 10 is able to instruct the imaging control section 11 (i.e., the imaging section 3 or the imaging signal processing section 15) to increase infrared imaging sensitivity to obtain image data of an infrared image as illustrated in FIG. 8B, in which a face of the child sleeping in the dark room and so on are recognizable.

Figure 9A:
FIGS. 9A and 9B are illustrations for describing an image photographed with increased ultraviolet sensitivity according to one embodiment of the present invention.
Figure 9B:

FIG. 9A illustrates an image obtained by regular imaging. In this case, the system controller 10 is able to instruct the imaging control section 11 (i.e., the imaging section 3 or the imaging signal processing section 15) to increase ultraviolet imaging sensitivity to obtain image data of an image as illustrated in FIG. 9B in which ultraviolet components are shown.

The imaging system is capable of obtaining the above types of image data including the image data of the image obtained by regular imaging. The image data in various states obtained by the imaging system are temporarily stored in the temporary storage section 23.

Needless to say, the image data that can be obtained by the imaging system is not limited to the above types of image data. Various other types of image data can also be obtained in various imaging modes by controlling processes performed by and the operations of the imaging section 3 and the imaging signal processing section 15.

A great variety of forms of photographed images are conceivable, such as: a telephoto image; a wide-angle image; an image photographed while zooming in or zooming out is performed within a range between a telephoto extreme and a wide-angle extreme; a magnified photographed image; a reduced photographed image; an image photographed with a varied frame rate (e.g., photographed with a high frame rate, or photographed with a low frame rate); a photographed image with increased brightness; a photographed image with reduced brightness; a photographed image with varied contrast; a photographed image with varied sharpness; an image photographed with increased imaging sensitivity; an image photographed with increased infrared imaging sensitivity; an image photographed with increased ultraviolet imaging sensitivity; an image photographed with a particular wavelength range cut off; effect-applied photographed images, such as a mosaic image, a brightness-reversed image, a soft-focus image, an image with a part of the image highlighted, and an image with varied overall color atmosphere; and a still photographed image.

4. Replay Operation

The replay operation will now be described below.

In the present embodiment, the image data obtained by constant imaging is stored in the temporary storage section 23, and the image data stored in the temporary storage section 23 can be used to present a replay display of a scene in the recent past. That is, it is possible to replay a past scene within a range of the image data stored in the temporary storage section 23.

In the case where the user witnessed a traffic accident by chance, for example, the user is able to watch a replay image of a scene of the accident. Further, while watching a sport game, the user is able to watch a replay image of a play in the immediate past.

Figure 11A:
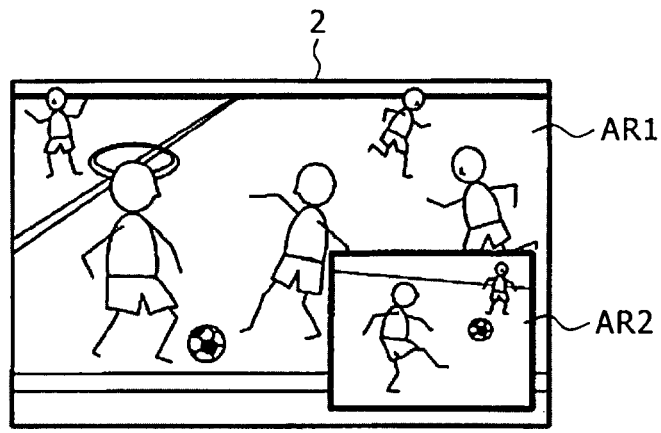
FIGS. 11A and 11B are illustrations for describing displaying of replay images according to one embodiment of the present invention.
Figure 11B:
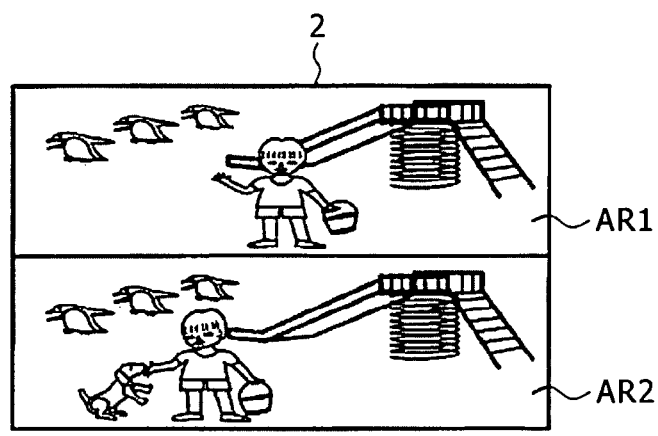

Examples of displays presented on the display section 2 at the time of the replay operation are illustrated in FIGS. 11A and 11B. At the time of the replay operation, the system controller 10 allows the image data to be read from the temporary storage section 23, and allows the read image data to be supplied to the display image processing section 12 via the image input/output control section 27. Then, the display image processing section 12 splits the screen of the display section 2, for example, and causes the replay image (i.e., the read image data) to be displayed on a part of the screen.

FIG. 11A illustrates an exemplary case where the display image processing section 12 has set a child-screen area AR2 within a parent-screen area AR1, and is displaying the replay image in the area AR2 while allowing the area AR1 to stay in the see-through state. In this case, the user is able to watch a replay image of a past scene with the area AR2 while seeing a current scene with the area AR1, which is in the see-through state.

FIG. 11B illustrates an exemplary case where the display image processing section 12 has split the screen into upper and lower areas AR1 and AR2, and is displaying the replay image in the area AR2 while allowing the area AR1 to stay in the see-through state. In this case also, the user is able to watch the replay image of the past scene with the area AR2 while seeing the current scene with the area AR1, which is in the see-through state.

As described above, the screen of the display section 2 is divided into the parent and child screens or split into two parts, for example, and the display of the replay image is presented while a part of the screen of the display section 2 is caused to stay in the see-through state. Needless to say, the position of the child screen within the screen and the size of the child screen may be changeable in accordance with the user operation. It is also possible that the screen of the display section 2 be split into left and right areas AR1 and AR2. It is also possible that the area of the area AR1 and the area of the area AR2 be set to be unequal by the user operation. Further, switching of display positions may be carried out in accordance with the user operation. For example, the parent screen and the child screen may be replaced by each other. Also, the areas obtained by screen splitting may be replaced by each other.

Further, instead of being caused to enter the see-through state, the area AR1 may be employed to display the image that is currently obtained by imaging by the imaging system (i.e., the image of the current scene, which is equivalent to the scene that the user would see if the screen were in the see-through state).

Still further, at the time of replaying, the replay image may be displayed on the entire screen of the display section 2. That is, the entire screen may be shifted from the see-through state (or a state in which the image obtained by regular imaging is being displayed) to a state in which the replay image is displayed.

Exemplary control exercised by the system controller 10 over the temporary storage section 23 when a request for replaying has been issued by the user operation will now be described below with reference to FIG. 10B.

FIG. 10B illustrates the storage area of the temporary storage section 23. As noted previously, the image data obtained by the imaging system constantly is sequentially stored between the top address AdST and the end address AdED of the storage area in the ring memory manner, while the write address pointer W-Ad is moving.

Suppose that the user has performed an operation to issue the request for replaying when the write address pointer W-Ad is pointing to an address AdX and the image data is being stored at the address AdX.

In this case, the system controller 10 continues incrementing of the write address pointer W-Ad and writing of the image data obtained by imaging, leaving the write address pointer W-Ad to continue to move forward from the address AdX. At the same time, the system controller 10 causes a read address pointer R-Ad to move backward from the address AdX. The temporary storage section 23 performs a process of reading image data at an address indicated by the read address pointer R-Ad, and the read image data is supplied to the display image processing section 12 via the image input/output control section 27 to be displayed in the area AR2 of the display section 2 as illustrated in FIGS. 11A and 11B, for example.

At this time, the speed of the read address pointer R-Ad may be changed (decremented) to 1.5 times speed, double speed, triple speed, or the like, so that images will be displayed on the display section 2 from the current scene to progressively earlier scenes in a fast reverse mode.

While watching the images played back in the fast reverse mode, the user, searching for the top of a scene that the user desires to replay, performs the replay start operation at a point at which the user desires replaying to start.

Suppose, for example, that the user has performed the replay start operation at a time when the read address pointer R-Ad has moved backward up to an address AdY. In this case, at the time when the user has performed the replay start operation, the system controller 10 causes the read address pointer R-Ad to start to be incremented in a normal moving direction and at a normal speed. As a result, the temporary storage section 23 starts to read the image data at the normal speed, starting with the address AdY, and accordingly, a series of replay images beginning with one stored at the address AdY starts to be displayed on the display section 2.

Suppose, for example, that the user has thereafter performed the replay termination operation when the read address pointer R-Ad has reached an address AdZ. In this case, the system controller 10 terminates replaying at this time. That is, the system controller 10 issues an instruction to terminate the reading in the temporary storage section 23 and the displaying of the replay images in the display section 2.

In this case, the images stored between the addresses AdY and AdZ correspond to the replay images which the user has desired to watch again.

While a simple example has been described above for purposes of illustration, it may happen that while the user is watching the images played back in the fast reverse mode, searching for the point at which the user desires replaying to start, fast reversing goes too far, and the user accordingly desires to fast-forward conversely. Also, the user may desire to watch the replay images not at the normal speed but at a low speed. Also, the user may desire to pause replaying or play some or all of the replay images repeatedly. Therefore, it is preferable that it be possible to change whether the read address pointer R-Ad is incremented or decremented in accordance with the user operation. It is also preferable that it be possible to change the rate of incrementing or decrementing or to pause replaying in accordance with the user operation.

Regarding the user operation, an operation unit related to replaying may be provided. Also, the system controller 10 may recognize a user behavior detected by the acceleration sensor or the like as the user operation, for example.

For example, the system controller 10 may regard the user's act of tapping the imaging apparatus 1 twice as the replay request operation and the replay termination operation. Also, the system controller 10 may regard the user's act of tapping the imaging apparatus 1 once as the replay start operation, for example.

Further, the user's act of tapping the imaging apparatus 1 from the left or right side may be regarded as an operation for fast-forwarding, an operation for fast-reversing, an operation for fast playback, an operation for slow playback, or the like. For example, the user's act of tapping the right side of the imaging apparatus 1 may be regarded as an operation for forward playback, and the user's act of tapping the left side of the imaging apparatus 1 as an operation for reverse playback, and the speed (slow, normal, double, etc.) of playback may be determined based on the number of times of tapping.

Needless to say, various other examples are conceivable. For example, the user's act of shaking his or her head may be regarded as an operation for fast-forwarding/fast-reversing.

In FIG. 10B, the user searches first the image of the current scene and then the images of the progressively earlier scenes to find the point at which the user desires replaying to be started. However, it may be so arranged that, when the user has performed a replay operation, replaying is started with an image of a scene a specified time ago. Also, it may be so arranged that the user is able to specify, by the number of times of tapping or the like, the point at which replaying is started, such as thirty seconds ago, one minute ago, three minutes ago, five minutes ago, and so on.

5. Exemplary Manners for Selecting Image to be Stored

As described above, the system controller 10 makes a determination concerning the storage condition and, when the storage condition has been satisfied, extracts the image data from the temporary storage section 23 to perform the storage process (i.e., the recording of the extracted image data in the storage section 25, or the transmission of the extracted image data to the external device via the communication section 26). Here, examples of the storage condition and the range of images that are extracted in response to the satisfaction of such storage conditions will be described.

Execution of Replaying

The user will perform the replay operation when the user has become interested in a scene that he or she viewed in the immediate past or when he or she desires to view the scene again for some reason. Therefore, the system controller 10 may determine that the storage condition has been satisfied when the replay operation has been performed in accordance with the user operation. In this case, the images that the user has watched again during the replay operation may be extracted as images to be stored. In the case of the example of FIG. 10B described above, for example, the image data stored in the range between the addresses AdY and AdZ is extracted as the images to be stored.

Operation Related to Imaging System

The user is able to perform an operation to instruct the imaging system to perform telephoto/wide-angle zooming, image magnification/reduction, imaging with increased infrared sensitivity, imaging with increased ultraviolet sensitivity, change of the frame rate, application of the image effect, or the like. It is reasonable to think that the user performs such an operation when he or she is viewing a scene that interests him or her. Therefore, the system controller 10 may determine that the storage condition has been satisfied when the user has performed such an operation related to the imaging system, so that an operation such as the telephoto/wide-angle zooming or the like or signal processing has been performed in the imaging system. In this case, image data obtained during a period in which the operation such as the telephoto/wide-angle zooming or the like or the signal processing continues to be performed may be extracted as images to be stored.

Determination Based on Biological Information (Occurrence of Biological Trigger)

It is possible to detect a state of the user, such as a state of tension, an excited state, or a comfortable state, based on the biological information detected by the biological sensor 21. The system controller 10 may determine that the storage condition has been satisfied when it has been determined that the user is in the state of tension or the like. This is because a scene that the user is viewing at that time can be considered as giving some stimulus to senses of the user. A reaction of the user indicated by the biological information detected when he or she has got excited or gone wild with excitement while watching a sport game, when he or she has witnessed a traffic accident or the like, when he or she has encountered a favorite person, celebrity, or the like, when he or she has got uneasy or afraid, or when he or she has been surprised, for example, may be regarded as a trigger for the satisfaction of the storage condition. This makes it possible to store a scene important for the user.

In the case where the user has been excited continuously for a certain period, image data obtained during that period, in which biological information indicating that the user is in the excited state continues to be obtained, may be extracted as images to be stored. In the case where biological information indicating that the user has been surprised for a moment has been obtained, image data obtained during a certain period around that moment may be extracted as images to be stored.

While the excited state can be detected by the biological information concerning the user, such as the brain waves, the blood pressure, or the galvanic skin response, the state of the user can also be determined based on the state of the pupil or movement of the line of sight detected by the visual sensor. Moreover, the motion of the body of the user detected by the acceleration sensor, the vibration sensor, or the like may be used to determine the state of the user.

Increase of the pulse or the like is sometimes caused by tension or excitement and other times by exercise such as running. In order to discriminate between such causes, information obtained by the acceleration sensor or the like may be additionally referred to.

Determination Based on External Sound (Occurrence of Sound Trigger)

The system controller 10 may determine that the storage condition has been satisfied when the audio analysis section 24, while analyzing the external sound, has detected occurrence of a very loud sound, such as a great cheer, a sound of an accident, or a warning sound, or occurrence or a specific sound. That is, the detection of the occurrence of such a sound may be regarded as a trigger for the satisfaction of the storage condition.

It may be so arranged that a specific sound, such as a voice of an acquaintance, an electronic sound, a cry of a pet, or a natural sound, is registered in the audio analysis section 24, and that the system controller 10 determines that the storage condition has been satisfied when the registered specific sound has been detected.

In such cases also, image data obtained during a period in which such a sound that causes the storage condition to be satisfied continues to be detected or image data obtained during a certain period around a time at which it is determined that the storage condition has been satisfied may be extracted as images to be stored.

Examples of the determination of the scene that has interested the user or the scene that the user desires to watch again, i.e., the determination concerning the storage condition, have been cited above. It should be noted, however, that there are many other manners for making a determination concerning the storage condition.

6. Exemplary Procedures

Exemplary control procedures performed by the system controller 10 for achieving the operations of the imaging apparatus 1 according to the present embodiment will now be described below. It is assumed here that the imaging apparatus 1 that has the display section 2 arranged in front of the eyes of the user as illustrated in FIG. 1 is used.

Figure 12:
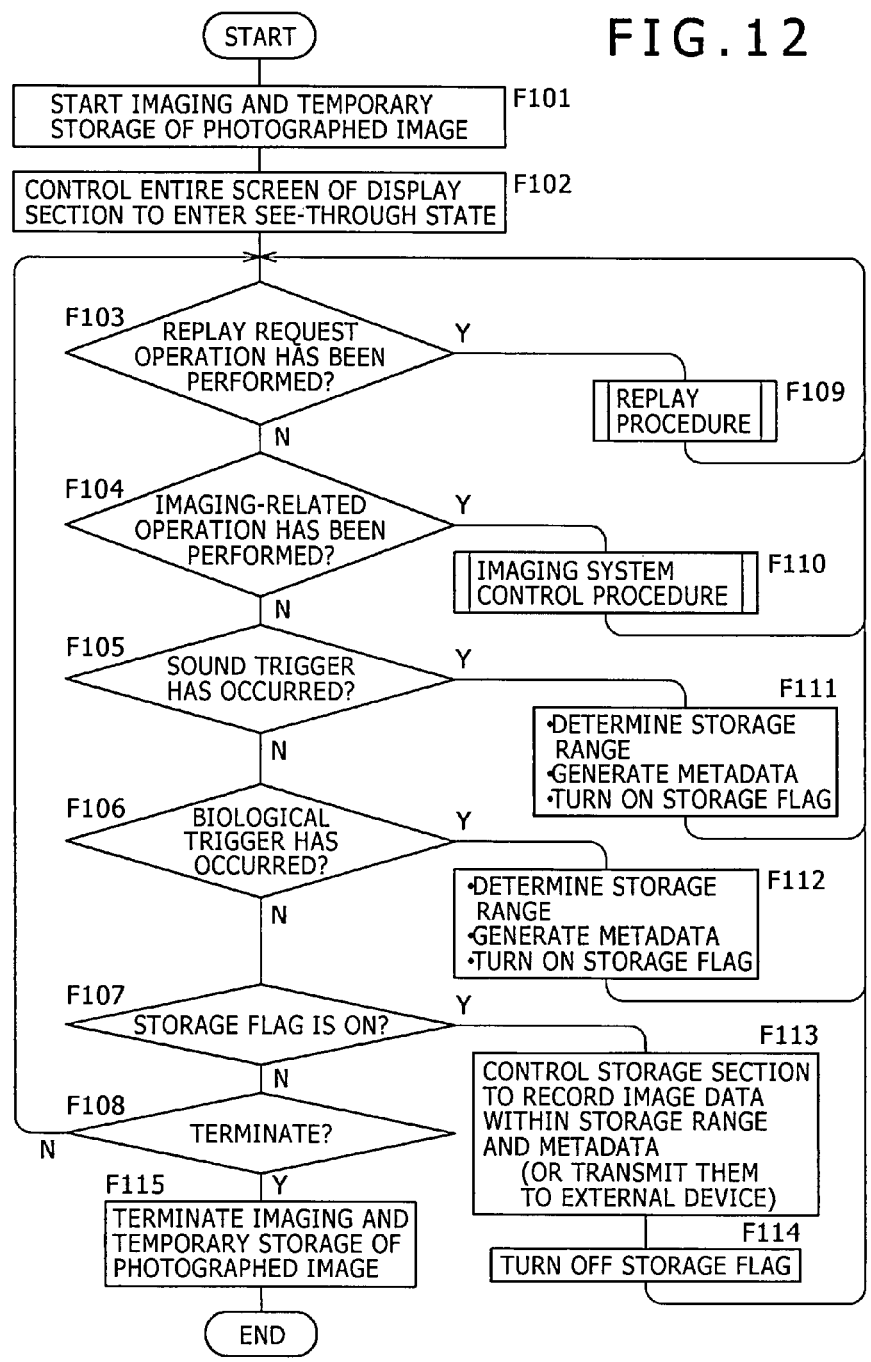
FIG. 12 is a flowchart illustrating a control procedure according to one embodiment of the present invention.

FIG. 12 illustrates a procedure performed by the system controller 10 between turn-on and turn-off of the imaging apparatus 1, for example. This procedure may also be considered as a procedure to be performed between a time when the user has performed an operation for starting the operation after the turn-on of the imaging apparatus 1 and a time when the user has performed an operation for terminating the operation.

In the case where the operation is started as a result of the turn-on of the imaging apparatus 1 or the like, the system controller 10 first starts imaging and the temporary storage of the image data obtained by imaging at step F101. Specifically, the system controller 10 controls the imaging system to start a regular imaging operation, allows the image data obtained by imaging to be supplied to the temporary storage section 23, and controls the temporary storage section 23 to start a storage operation in the ring memory manner.

Thereafter, this imaging and the storage of the image data obtained by imaging in the temporary storage section 23 are continued until the operation is terminated as a result of the turn-off of the imaging apparatus 1 or the like.

At step F102, the system controller 10 instructs the display control section 14 to cause the entire screen of the display section 2 to enter the see-through state.

As a result of the processes of steps F101 and F102, the user becomes able to view the scene within his or her field of vision in a regular manner through the display section 2, which is in the see-through state, and the scenes within the user's field of vision are constantly imaged and temporarily stored.

After the operation is started in the above-described manner, the system controller 10 performs monitoring processes in a monitoring process loop at steps F103, F104, F105, F106, F107, and F108.

At step F103, the system controller 10 monitors whether the user has performed an operation for requesting replaying.

At step F104, the system controller 10 monitors whether the user has performed an imaging-related operation. The term "imaging-related operation" as used herein refers to an operation for switching the image data obtained by the imaging system from the image data obtained by regular imaging to another type of image data. Examples of such operations include a telephoto/wide-angle zoom operation, an operation for image magnification/reduction, an operation for adjusting the imaging frame rate, an operation for changing the imaging sensitivity, an operation for increasing the infrared imaging sensitivity, an operation for increasing the ultraviolet imaging sensitivity, and an operation for image processing such as the application of the image effect. Further, an operation for shifting the state of imaging from such a non-regular state back to a regular state is also one example of the imaging-related operations.

At step F105, the system controller 10 monitors based on the information obtained from the audio analysis section 24 whether a sound trigger (the satisfaction of the storage condition as a result of audio analysis) has occurred.

At step F106, the system controller 10 monitors based on the information obtained from the biological sensor 21 whether a biological trigger (i.e., the satisfaction of the storage condition based on the biological information) has occurred.

At step F107, the system controller 10 determines whether an internal storage flag is on.

At step F108, the system controller 10 monitors whether the operation should be terminated as a result of a turn-off operation or the operation for terminating the operation being performed by the user, for example.

Figure 13:
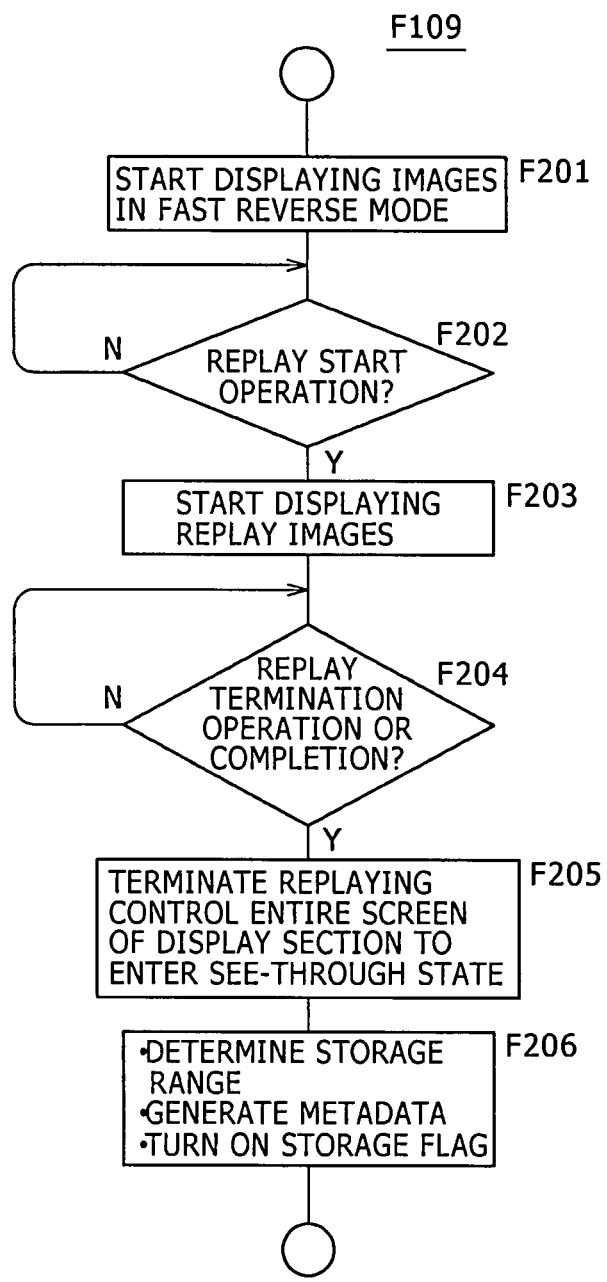
FIG. 13 is a flowchart illustrating a replay procedure according to one embodiment of the present invention.

When the user has performed the replay request operation, the system controller 10 proceeds from step F103 to step F109, and performs a replay procedure. This replay procedure is a procedure for executing the operation described above with reference to FIG. 10B, and is illustrated in FIG. 13.

First, at step F201, the system controller 10 performs control for starting the displaying of the images in the fast reverse mode. Specifically, the system controller 10 controls the temporary storage section 23 to read the image data while decrementing the read address pointer R-Ad so as to move backward from a current location of the write address pointer W-Ad approximately at the double speed, for example. In addition, the system controller 10 instructs the display control section 14 to allow the image data read from the temporary storage section 23 to be displayed on a part of the screen, such as the area AR2 as illustrated in FIG. 11A or 11B. Note that the images played back in the fast reverse mode may be displayed on the entire screen of the display section 2.

As a result of the process of step F201, the user becomes able to watch the images played back in the fast reverse mode (i.e., the image of the current scene and the images of the progressively earlier scenes). While watching the images played back in the fast reverse mode, the user searches for a start point of the scene that the user desires to watch again, and performs the replay start operation at the start point.

Upon detection of the replay start operation, the system controller 10 proceeds from step F202 to step F203, and performs control for starting the displaying of the replay images. Specifically, the system controller 10 controls the temporary storage section 23 to change the mode of the read address pointer R-Ad so that the read address pointer R-Ad starts to be incremented (i.e., move in the normal direction in which time progresses) at the normal speed, and read the image data. As a result, the replay images are played back in a normal manner and displayed on the display section 2, and the user becomes able to watch the scene in the recent past again. Note that although not shown in FIG. 13, at this time, the replay images may be played back at a low speed or played back at a high speed such as the 1.5 times speed in accordance with the user operation.

When it is detected thereafter that the user has performed the replay termination operation or when replaying has been completed thereafter, the system controller 10 proceeds from step F204 to step F205. Replaying is completed, for example, when replaying has progressed so far as to reach the image that was obtained at the time when the user performed the replay request operation (i.e., the address that was indicated by the write address pointer W-Ad at the time when the user requested replaying) or when, in the case where replaying is performed at a high speed, replaying has progressed still further to reach an image that is obtained at the current time (i.e., an address that is indicated by the write address pointer W-Ad at the current time).

When the replay termination operation has been performed or when replaying has been completed, the system controller 10 performs a replay termination process at step F205. Specifically, the system controller 10 controls the temporary storage section 23 to terminate the reading of the image data, and instructs the display control section 14 to return the entire screen of the display section 2 to the see-through state.

As noted previously, the system controller 10 regards the performance of the replay operation as the satisfaction of the storage condition. Therefore, at step F206, the system controller 10 determines a storage range of the image data to be stored as an accompaniment to the performance of the replay operation. In addition, the system controller 10 generates the metadata. This metadata includes information representing that the image data to be stored has been determined because of the performance of the replay operation. Further, the system controller 10 turns on the storage flag.

After performing the above processes, the system controller 10 returns to the monitoring loop at steps F103 to F108 in FIG. 12.

Immediately after the above replay procedure is performed, the system controller 10 proceeds from step F107 to step F113 in FIG. 12 because the storage flag has been turned on. Then, at step F113, the system controller 10 performs the storage process.

As the storage process, the system controller 10 controls the storage section 25 to record the image data within the storage range and the metadata on the storage medium. That is, in this case, the system controller 10 allows the image data within the storage range determined at step F206 in FIG. 13, e.g., the image data that was displayed in replaying, to be transferred from the temporary storage section 23 to the storage section 25, and transmits the metadata generated at step F206 to the storage section 25. Then, the system controller 10 controls the storage section 25 to add the metadata to the image data, encode the resultant data for recording, and record the resultant data on the storage medium.

Note that the above control is performed in the case where the imaging apparatus 1 includes the storage section 25 as illustrated in FIG. 3, and that in the case where the imaging apparatus 1 includes the communication section 26 in place of the storage section 25 as illustrated in FIG. 4, the system controller 10 performs control for allowing the image data within the storage range and the metadata to be encoded for transmission, and transmitting the resultant data to the external device via the communication section 26.

After the storage process at step F113 is completed, the system controller 10 turns off the storage flag at step F114 and returns to the monitoring loop at steps F103 to F108.

Figure 14:
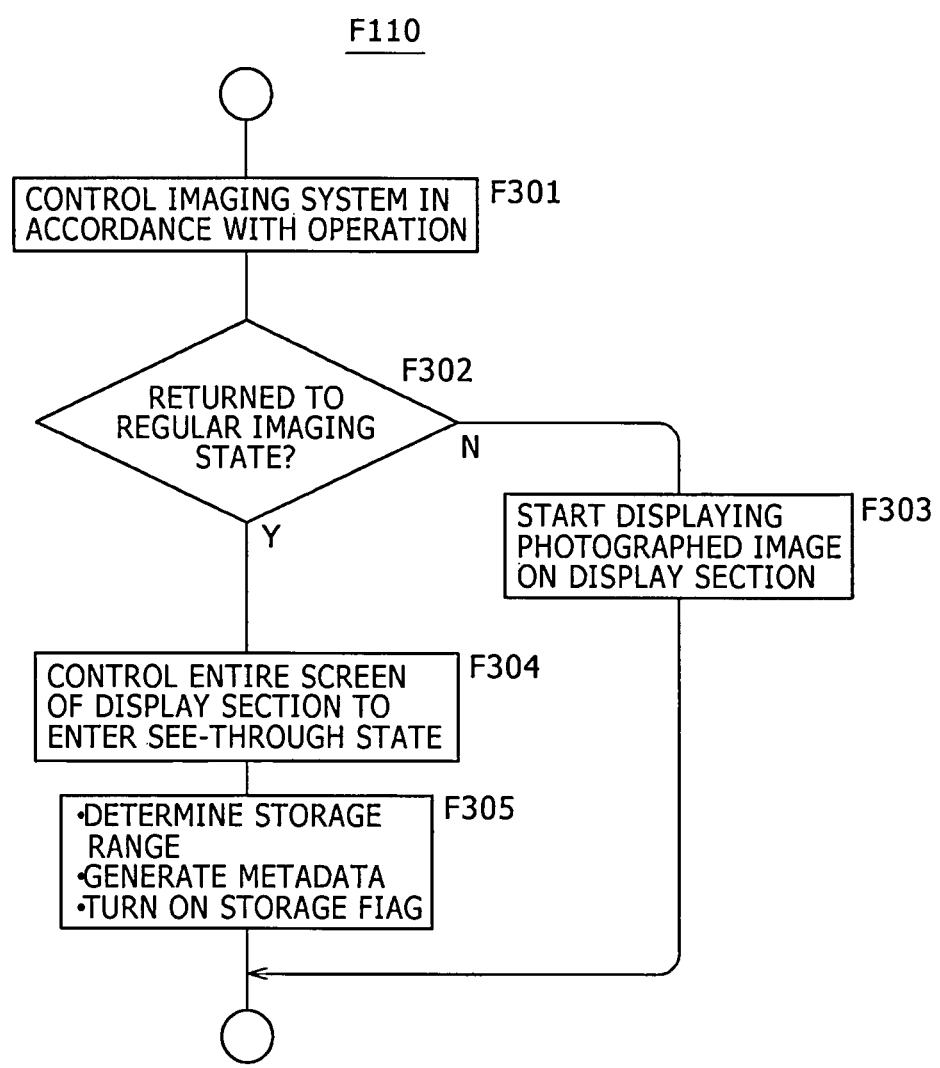
FIG. 14 is a flowchart illustrating an imaging system control procedure according to one embodiment of the present invention.

When the user has performed the imaging-related operation, the system controller 10 proceeds from step F104 to step F110, and performs an imaging system control procedure. The imaging system control procedure is illustrated in FIG. 14.

First, at step F301, the system controller 10 performs control related to the imaging system in accordance with the imaging-related operation. That is, the system controller 10 causes an operation requested by the user to be performed.

In the case where the user has performed the telephoto or wide-angle zoom operation, for example, the system controller 10 instructs the imaging control section 11 to perform the zoom operation and drive the zoom lens in the imaging section 3.

In the case where the user has performed the operation for image magnification or reduction, the system controller 10 instructs the imaging control section 11 to perform an image magnification or reduction process, thereby causing the imaging signal processing section 15 to perform the magnification process or the reduction process on the photographed image data.

In the case where the user has performed the operation for adjusting the imaging frame rate, the system controller 10 instructs the imaging control section 11 to change the frame rate, thereby changing the frame rate in the imaging section 3 and the imaging signal processing section 15.

In the case where the user has performed the operation for changing the imaging sensitivity, the operation for increasing the infrared imaging sensitivity, or the operation for increasing the ultraviolet imaging sensitivity, the system controller 10 instructs the imaging control section 11 to change the imaging sensitivity, thereby changing sensitivity of signals obtained from an imaging device in the imaging section 3 (e.g., changing a gain of the signals read from the imaging device).

In the case where the user has performed the operation for the application of the image effect, the system controller 10 instructs the imaging control section 11 to perform an effect process on the image, thereby causing the imaging signal processing section 15 to perform the image effect process on the photographed image data.

In the case where the user has performed an operation for shifting the state of imaging from any of the non-regular states such as, a telephoto/wide-angle zoom state, an image magnification/reduction state, a frame rate changing state, a sensitivity changing state, or an image effect state, back to the regular state, the system controller 10 instructs the imaging control section 11 to perform regular imaging, thereby returning the operations of the imaging section 3 and the imaging signal processing section 15 to the state in which regular imaging is performed.

As described above, the system controller 10 controls the operation of the imaging system in accordance with the imaging-related operation performed by the user. When, at step F301, the system controller 10 has controlled the operation of the imaging system, which has been imaging in the regular manner, so that the telephoto/wide-angle zooming, the image magnification/reduction, the change of the frame rate, the change of the sensitivity, the application of the image effect, or the like is performed, the system controller 10 proceeds from step F302 to step F303, and, in this case, the system controller 10 causes the photographed image to be displayed on the display section 2. That is, the system controller 10 controls the image input/output control section 27 to supply the image data obtained from the imaging system to the display image processing section 12 while continuing to supply the image data obtained from the imaging system to the temporary storage section 23 as before, and also instructs the display control section 14 to display the photographed image data.

Then, the system controller 10 returns to the monitoring loop at steps F103 to F108.

Hereinafter, in order to facilitate description, a state of the imaging operation in which the telephoto/wide-angle zooming, the image magnification/reduction, the change of the frame rate, the change of the sensitivity, the application of the image effect, or the like is performed will be referred to as a "special imaging state", and thus be differentiated from a regular imaging state. The regular imaging state refers to a state of the imaging operation in which the image equivalent to the image viewed through the display section 2 in the see-through state is obtained, as illustrated in FIG. 6B.

When the user has performed an operation for shifting the state of the imaging operation to the special imaging state, such as the zoom operation, the process of step F303 causes the display section 2 to switch from the see-through state to a state in which a zoom image or the like is displayed, so that the user becomes able to view the photographed image. That is, if the user performs the operation for the telephoto/wide-angle zooming, the image magnification/reduction, the change of the frame rate, the change of the imaging sensitivity, imaging with increased infrared sensitivity, imaging with increased ultraviolet sensitivity, the application of the image effect, or the like, the user becomes able to view a corresponding photographed image (e.g., one of the images as described above with reference to FIGS. 6A to 9B) obtained in the special imaging state with the display section 2.

Note that, in this case, the photographed image may be displayed on the entire screen of the display section 2, or as is the case with the replay images as illustrated in FIGS. 11A and 11B, the photographed image may be displayed in a part of the screen such as the area AR2 while the area AR1 is in the see-through state.

In the case where the imaging-related operation detected at step F103 is an operation for shifting the state of the imaging operation from the special imaging state back to the regular imaging state, the system controller 10 controls the imaging system to return to the regular imaging state at step F301 in FIG. 14 as described above. In this case, the system controller 10 proceeds from step F302 to step F304.

At step F304, the system controller 10 instructs the display control section 14 to control the entire screen of the display section 2 to return to the see-through state.

The system controller 10 regards the shifting of the state of the imaging operation to the special imaging state as a result of the user operation as the satisfaction of the storage condition. Therefore, at step F305, the system controller 10 determines the storage range of the image data to be stored in accordance with special imaging that had been performed up to the immediate past. In addition, the system controller 10 generates the metadata. This metadata includes information indicating that the image data to be stored has been determined because of the special imaging state, such as information that indicates, as special imaging that had been performed, telephoto zooming, wide-angle zooming, image magnification, image reduction, the change of the frame rate, the change of the imaging sensitivity, imaging with increased infrared sensitivity, imaging with increased ultraviolet sensitivity, the application of the image effect, or the like.

Further, the system controller 10 turns on the storage flag.

After performing the above processes, the system controller 10 returns to the monitoring loop at steps F103 to F108 in FIG. 12.

Immediately after the state of the imaging operation is shifted from the special imaging state back to the regular imaging state, the system controller 10 proceeds from step F107 to step F113 in FIG. 12 because the storage flag has been turned on. Then, at step F113, the system controller 10 performs the storage process.

As the storage process, the system controller 10 controls the storage section 25 to record the image data within the storage range and the metadata on the storage medium. That is, in this case, the system controller 10 allows the image data within the storage range determined at step F305 in FIG. 14, e.g., the image data that was obtained by imaging in the special imaging state, to be transferred from the temporary storage section 23 to the storage section 25, and transmits the metadata generated at step F305 to the storage section 25. Then, the system controller 10 controls the storage section 25 to add the metadata to the image data, encode the resultant data for recording, and record the resultant data on the storage medium.

Note that in the case where the imaging apparatus 1 includes the communication section 26, the system controller 10 may perform control for allowing the image data within the storage range and the metadata to be encoded for transmission, and transmitting the resultant data to the external device via the communication section 26.

After the storage process at step F113 is completed, the system controller 10 turns off the storage flag at step F114 and returns to the monitoring loop at steps F103 to F108.

Incidentally, the special imaging state may continue for a long time. For example, a zoom state or the like may continue longer than a period of time for which the data is stored in the temporary storage section 23. Note that this period of time depends on a storage capacity of the temporary storage section 23. Therefore, if the storage process is performed at step F113 after the state of imaging is returned to the regular imaging state, for example, part of the image data to be stored may have already been lost.

Therefore, it may be necessary to modify the above procedures so that when a certain period of time has elapsed after the state of imaging was shifted to the special imaging state, the processes of steps F305 and F113 will be performed interruptively.

Moreover, although not shown in FIG. 14, it may happen that the state of imaging is switched from a certain special imaging state to another special imaging state or that a compound operation is requested. For example, the state of imaging may be switched from a telephoto zoom state to a state in which imaging is performed with a varied frame rate. Also, imaging with increased infrared sensitivity may be requested while the telephoto zoom state should be maintained. It is preferable that the processes of steps F305 and F113 be performed interruptively when the mode of the operation has been altered while the state of imaging is maintained in the special imaging state.

When the system controller 10 has determined that the sound trigger has occurred in the monitoring loop at steps F103 to F108, the system controller 10 proceeds from step F105 to step F111. Then, the system controller 10 determines the storage range of the image data to be stored as an accompaniment to the occurrence of the sound trigger. In addition, the system controller 10 generates the metadata. This metadata includes information representing that the image data to be stored has been determined because of the occurrence of the sound trigger, and a content of the sound trigger (i.e., the analysis information obtained by the audio analysis section 24). Further, the system controller 10 turns on the storage flag.

After performing the above processes, the system controller 10 returns to the monitoring loop at steps F103 to F108. Immediately after this, the system controller 10 proceeds from step F107 to step F113 because the storage flag has been turned on, and performs the storage process.

As the storage process, the system controller 10 controls the storage section 25 to record the image data within the storage range and the metadata on the storage medium. That is, in this case, the system controller 10 allows the image data within the storage range determined at step F111 to be transferred from the temporary storage section 23 to the storage section 25, and transmits the metadata generated at step F111 to the storage section 25. Then, the system controller 10 controls the storage section 25 to add the metadata to the image data, encode the resultant data for recording, and record the resultant data on the storage medium.

In the case where the imaging apparatus 1 includes the communication section 26, the system controller 10 may perform control for allowing the image data within the storage range and the metadata to be encoded for transmission, and transmitting the resultant data to the external device via the communication section 26.

After the storage process at step F113 is completed, the system controller 10 turns off the storage flag at step F114 and returns to the monitoring loop at steps F103 to F108.

When the system controller 10 has determined that the biological trigger has occurred in the monitoring loop at steps F103 to F108, the system controller 10 proceeds from step F106 to step F112. Then, the system controller 10 determines the storage range of the image data to be stored as an accompaniment to the occurrence of the biological trigger. In addition, the system controller 10 generates the metadata. This metadata includes information representing that the image data to be stored has been determined because of the occurrence of the biological trigger, and a content of the biological trigger (e.g., the information detected by the biological sensor 21, a content of judgment about the state of the user based on the detected information, etc.). Further, the system controller 10 turns on the storage flag.

After performing the above processes, the system controller 10 returns to the monitoring loop at steps F103 to F108. Immediately after this, the system controller 10 proceeds from step F107 to step F113 because the storage flag has been turned on, and performs the storage process.

As the storage process, the system controller 10 controls the storage section 25 to record the image data within the storage range and the metadata on the storage medium. That is, in this case, the system controller 10 allows the image data within the storage range determined at step F112 to be transferred from the temporary storage section 23 to the storage section 25, and transmits the metadata generated at step F112 to the storage section 25. Then, the system controller 10 controls the storage section 25 to add the metadata to the image data, encode the resultant data for recording, and record the resultant data on the storage medium.

In the case where the imaging apparatus 1 includes the communication section 26, the system controller 10 may perform control for allowing the image data within the storage range and the metadata to be encoded for transmission, and transmitting the resultant data to the external device via the communication section 26.

After the storage process at step F113 is completed, the system controller 10 turns off the storage flag at step F114 and returns to the monitoring loop at steps F103 to F108.

When the power is turned off or the operation is completed, the system controller 10 proceeds from step F108 to step F115, and terminates the imaging operation in the imaging system and the storage of the image data in the temporary storage section 23, thereby finishing the series of processes.

According to the above-described procedures, the constant imaging and the temporary storage of the image data obtained by imaging are performed while, out of the image data temporarily stored, the image data of the image that has interested the user or which the user desires to watch again later is stored in the storage section 25 on a permanent basis (or transmitted to the external device via the communication section 26 and stored therein on a permanent basis).

Moreover, the user is able to watch the scene that he or she viewed in the immediate past by the replay operation.

Note that it has been assumed in the above-described exemplary procedures that the images are displayed on a part or the whole of the display section 2 when the imaging system has entered the special imaging state or when the displaying of the replay images is performed, while otherwise the entire screen of the display section 2 is caused to stay in the see-through state. However, instead of causing the entire screen of the display section 2 to stay in the see-through state, it is possible to display the image data obtained by regular imaging on the entire screen of the display section 2.

Also note that in the case where, as illustrated in FIG. 2, the imaging apparatus 1 is composed of the display apparatus section 30 and the imaging apparatus section 40, which are separate from each other, a process of causing the display apparatus section 30 to enter the see-through state does not need to be performed. In this case, it may be so arranged that, at normal times, the screen of the display apparatus section 30 stays inactive or the image data obtained by regular imaging is displayed thereon.

7. Imaging Apparatus Dedicated to Replaying

The imaging apparatus 1 according to the present embodiment as described above has the capability to store the image data of the scene that has interested the user in his or her daily life on a permanent basis. By contrast, an imaging apparatus that is simply capable of replaying, for example, the scene that interested the user in the immediate past is also conceivable.

An imaging apparatus 1A dedicated to replaying will now be described below with reference to FIGS. 15 and 16.

Figure 15:
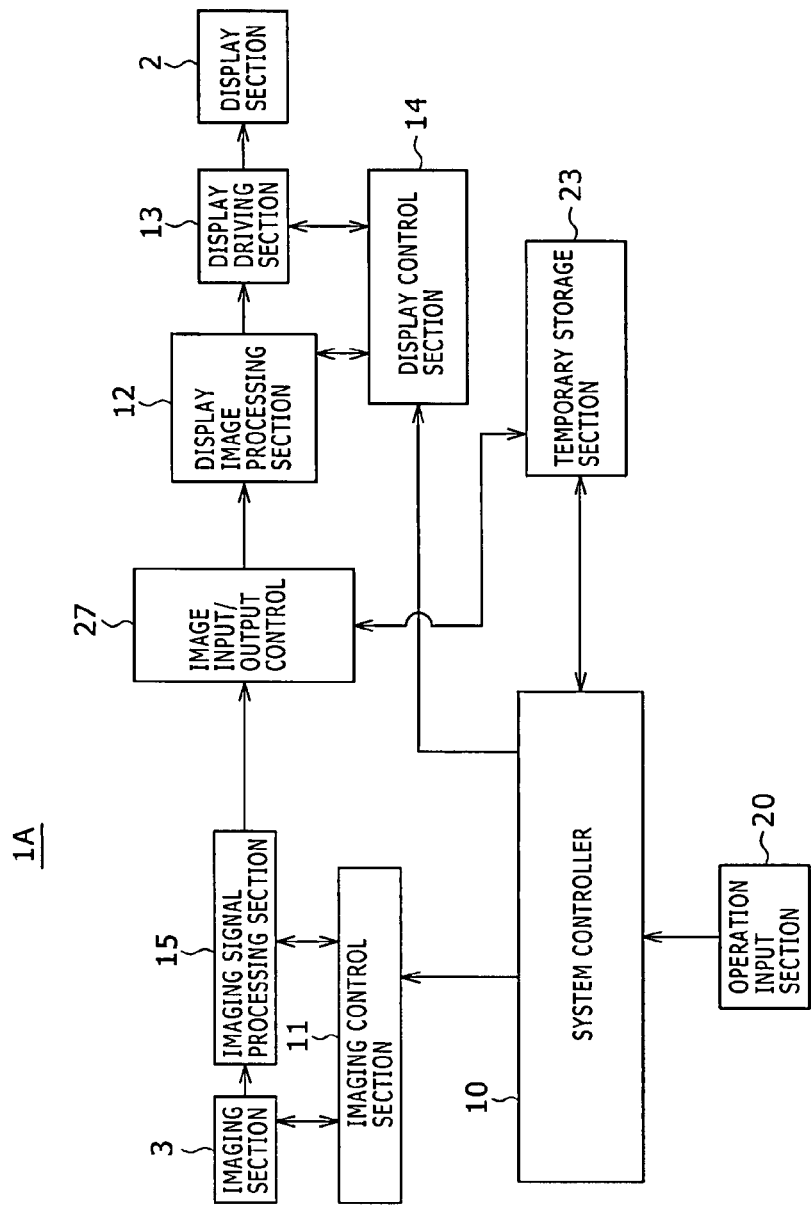
FIG. 15 is a block diagram of an imaging apparatus dedicated to replaying according to one embodiment of the present invention.
Figure 16:
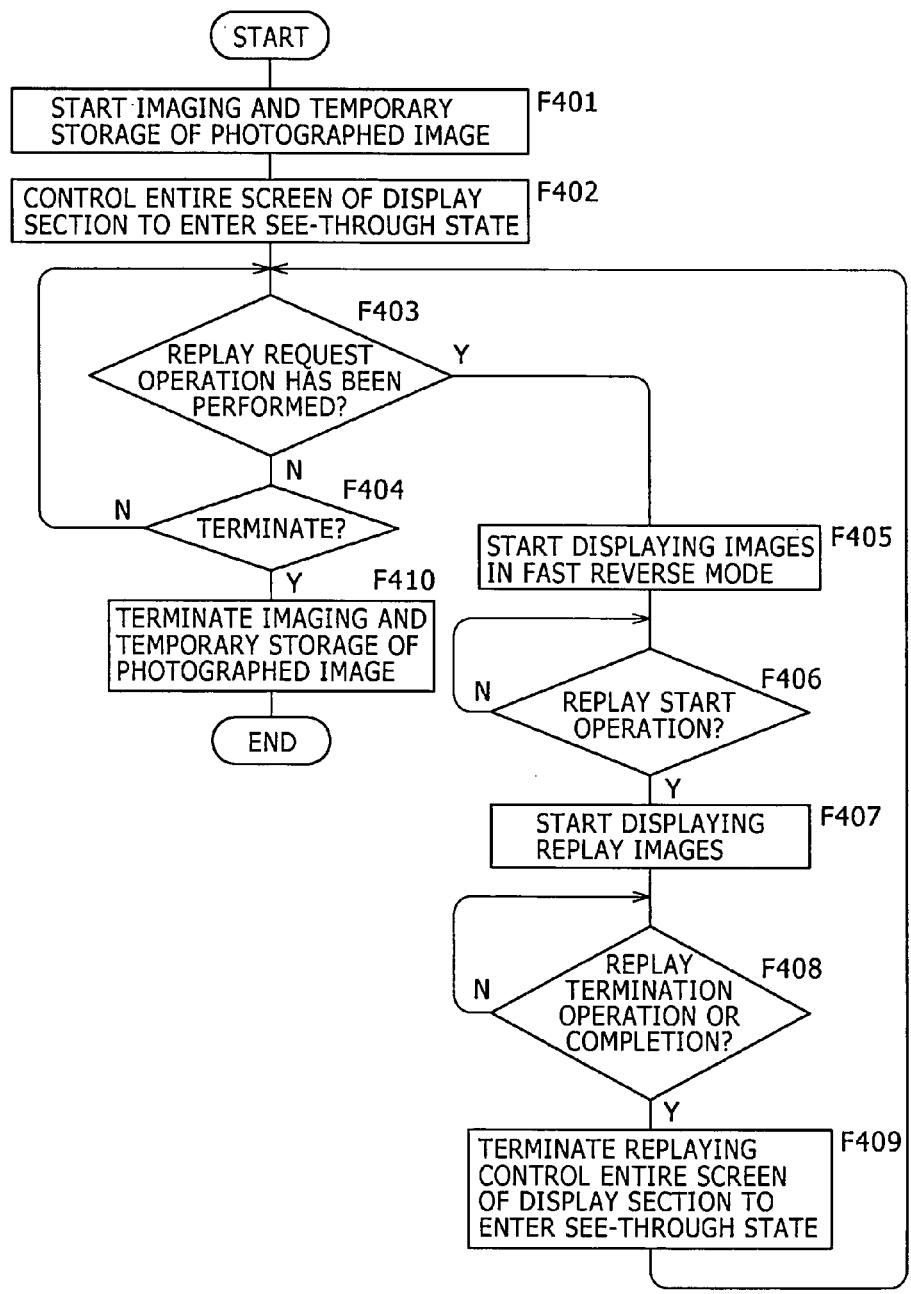
FIG. 16 is a flowchart illustrating a procedure performed by the imaging apparatus dedicated to replaying according to one embodiment of the present invention.

FIG. 15 illustrates an exemplary structure of the imaging apparatus 1A dedicated to replaying. Note that in FIG. 15, components that have their counterparts in FIG. 3, 4, or 5 are assigned the same reference numerals as those of their counterparts in FIG. 3, 4, or 5, and descriptions thereof will be omitted. The imaging apparatus 1A includes the system controller 10, the imaging section 3, the imaging signal processing section 15, the imaging control section 11, the image input/output control section 27, the display image processing section 12, the display driving section 13, the display control section 14, the display section 2, the temporary storage section 23, and the operation input section 20. That is, the imaging apparatus 1A is different from the imaging apparatus 1 illustrated in FIG. 3 in that the audio input section 6, the audio analysis section 24, the audio input/output control section 28, the audio signal processing section 16, the audio output section 5, the storage section 25, and the biological sensor 21 are omitted.

The imaging system (i.e., the imaging section 3, the imaging signal processing section 15, and the imaging control section 11) performs constant imaging, and the image data obtained by the constant imaging is supplied to the temporary storage section 23 via the image input/output control section 27 and stored temporarily in the temporary storage section 23.

When the user has performed the replay operation via the operation input section 20, the image data temporarily stored in the temporary storage section 23 is read therefrom and supplied to the display image processing section 12, and the replay images are displayed on the display section 2.

A procedure performed by the system controller 10 of the imaging apparatus 1A will now be described below with reference to FIG. 16.

In the case where the operation is started as a result of the turn-on of the imaging apparatus 1A or the like, the system controller 10 first starts imaging and the temporary storage of the image data obtained by imaging at step F401. Specifically, the system controller 10 controls the imaging system to start the regular imaging operation, allows the image data obtained by imaging to be supplied to the temporary storage section 23, and controls the temporary storage section 23 to start the storage operation in the ring memory manner.

Thereafter, this imaging and the storage of the image data obtained by imaging in the temporary storage section 23 are continued until the operation is terminated as a result of the turn-off of the imaging apparatus 1A or the like.

At step F402, the system controller 10 instructs the display control section 14 to cause the entire screen of the display section 2 to enter the see-through state.

After the operation is started in the above-described manner, the system controller 10 performs a monitoring process in a monitoring process loop at steps F403 and F404.

At step F403, the system controller 10 monitors whether the user has performed the replay operation.

At step F404, the system controller 10 monitors whether the operation should be terminated as a result of a power turn-off operation or the operation for terminating the operation being performed by the user, for example.

When the user has performed the replay request operation, the system controller 10 proceeds from step F403 to step F405, and starts the replay procedure.

First, at step F405, the system controller 10 performs control for starting the displaying of the images in the fast reverse mode. Specifically, the system controller 10 controls the temporary storage section 23 to read the image data while decrementing the read address pointer R-Ad so as to move backward from a current location of the write address pointer W-Ad approximately at the double speed, for example. In addition, the system controller 10 instructs the display control section 14 to allow the image data read from the temporary storage section 23 to be displayed on a part of the screen, such as the area AR2 as illustrated in FIG. 11A or 11B. Note that the images played back in the fast reverse mode may be displayed on the entire screen of the display section 2.

As a result of the process of step F405, the user becomes able to watch the images played back in the fast reverse mode (i.e., the image of the current scene and the images of the progressively earlier scenes). While watching the images played back in the fast reverse mode, the user searches for the start point of the scene that the user desires to watch again, and performs the replay start operation at the start point.

Upon detection of the replay start operation, the system controller 10 proceeds from step F406 to step F407, and performs control for starting the displaying of the replay images. Specifically, the system controller 10 controls the temporary storage section 23 to change the mode of the read address pointer R-Ad so that the read address pointer R-Ad starts to be incremented (i.e., move in the normal direction in which time progresses) at the normal speed, and read the image data. As a result, the replay images are played back in the normal manner and displayed on the display section 2, and the user becomes able to watch the scene in the recent past again. Note that, at this time, the replay images may be played back at a low speed or played back at a high speed such as the 1.5 times speed in accordance with the user operation.

When it is detected thereafter that the user has performed the replay termination operation or when replaying has been completed thereafter, the system controller 10 proceeds from step F408 to step F409, and performs the replay termination process. Specifically, the system controller 10 controls the temporary storage section 23 to terminate the reading of the image data, and instructs the display control section 14 to return the entire screen of the display section 2 to the see-through state.

After performing the above processes, the system controller 10 returns to the monitoring loop at steps F403 and F404.

When the power is turned off or the operation is completed, the system controller 10 proceeds from step F404 to step F410, and terminates the imaging operation in the imaging system and the storage of the image data in the temporary storage section 23, thereby finishing the series of processes.

According to the above-described procedure, the constant imaging and the temporary storage of the image data obtained by imaging are performed while when the user desires to watch the scene in the immediate past again, the user can watch the scene again which he or she viewed in the immediate past by performing the replay operation. That is, the imaging apparatus 1A is an imaging apparatus capable of displaying the replay images when the user desires to watch them, despite its simple structure.

Note that it has been assumed in the above exemplary procedure that the images are displayed on a part or the whole of the display section 2 when the displaying of the replay images is performed, while otherwise the entire screen of the display section 2 is caused to stay in the see-through state. However, instead of causing the entire screen of the display section 2 to stay in the see-through state, it is possible to display the image data obtained by imaging by the imaging system on the entire screen of the display section 2.

Also note that in the case where, as illustrated in FIG. 2, the display apparatus section 30 is provided independently, a process of causing the display apparatus section 30 to enter the see-through state does not need to be performed. In this case, it may be so arranged that, at normal times, the screen of the display apparatus section 30 stays inactive or the image data obtained by imaging by the imaging system is displayed thereon.

8. Effects of Embodiments

In the imaging apparatus 1 according to the above-described embodiments of the present invention, image data of scenes that the user sees in his or her daily life is stored temporarily while, when the predetermined storage condition has been satisfied, the storage process of storing the image data together with the metadata is performed.

Therefore, it is possible to extract, from the image data of such daily scenes obtained by constant imaging, the image data of the scene that interests the user or the scene that the user desires to watch again later, and store the extracted image data properly to make the image data available for use. Moreover, the metadata added to the stored image data is useful in searching for a desired image (scene) when using the stored image data later.

More specifically, the following is made possible.

In the imaging apparatus 1 according to the above-described embodiment of the present invention, every scene that the user sees is stored temporarily. Therefore, the user is able to watch the scene in the immediate past again by replaying.

In the case where the user is watching a sport game in a sports ground, a soccer stadium, a ballpark, or the like, for example, the user is normally unable to watch a replay as when the user is watching a sport game with a television broadcast. However, if the user wears the imaging apparatus 1, the user is able to watch a replay of a play of a player arbitrarily, for example.

Further, it may happen that, in his or her daily life, the user is absentminded and misses a certain scene, the user happens to pass an interesting person, or the user witnesses a traffic accident or the like. In such cases, as well as in various other cases, the user is able to watch a scene in the immediate past by replaying.

Because the temporary storage section 23 is assumed to be used for temporary storage, the temporary storage section 23 can be used for storing the images constantly obtained by imaging, using its storage area in the ring memory manner, and does not need to have enormous storage capacity. The storage capacity of the temporary storage section 23 may be determined in a design stage based on how long ago the image data that can be replayed should extend, for example.

Further, by performing the imaging-related operation, the user is able to watch the image obtained by imaging in the special imaging state with the display section 2, such as the telephoto image, the wide-angle image, the magnified image, the image photographed with increased infrared imaging sensitivity, the image photographed with increased ultraviolet imaging sensitivity, or the image photographed with a high frame rate. Thus, the user is able to arbitrarily watch a scene that may not be seen with a normal vision.

Further, when the user has performed an operation to issue an instruction to perform replaying or imaging in the special imaging state, a scene that is a subject of replaying or imaging is probably an interesting scene for the user. Since the storage process of causing the image data of such a scene to be stored in the storage section 25 (or the external device with which the communication section 26 communicates) on a permanent basis is performed, the image of the interesting scene for the user is stored. Therefore, the user is able to play the image of the scene at a later date to watch the scene again. The user is also able to compile such stored images into a video album or the like that records an action history or memories of the user, for example.

Similarly, the biological trigger, the sound trigger, and the like also initiate the storage process of storing the image data. Therefore, without the need for the user to perform any particular operation, the image data of the scene that interests the user or which is important for the user can be stored on a permanent basis.

Thus, an imaging apparatus that is capable of recording the image of the important scene in the user's daily life is achieved.

It should be understood by those skilled in the art that various modifications, combinations, sub-combinations and alterations may occur depending on design requirements and other factors insofar as they are within the scope of the appended claims or the equivalents thereof.

What is claimed is:

1. An imaging apparatus, comprising:
   one rigid, head-wearable unit substantially in the shape of eye glasses that includes an acceleration sensor;
   imaging means for imaging at least one scene in a forward direction in which a user sees to obtain image data of the at least one scene;
   temporary storage means using a storage area in a ring memory manner for storing continuously the image data obtained by said imaging means;
   means for executing a selected imaging operation from a plurality of active imaging operations responsive to detecting with the acceleration sensor a tapping pattern corresponding to the selected imaging operation applied by a user to the head-wearable unit; and
   control means for automatically causing, responsive to at least one predetermined storage condition of a plurality of predetermined storage conditions being satisfied:
      extraction of selected image data from the image data stored in temporary storage means,
      storage of the selected image data in semi-permanent storage, and
      association of metadata with the selected image data,
      wherein the metadata includes information about the at least one predetermined storage condition that caused the extraction and storage of the selected image data.

2. The imaging apparatus according to claim 1, wherein said temporary storage means stores image data beginning at a start address, moving sequentially to an end address, and returning to the start address cyclically.

3. The imaging apparatus according to claim 1, further comprising:
   storage means for storing data in a nonvolatile storage medium;
   wherein said control means performs a process of controlling said storage means to store the selected image data and the metadata in the nonvolatile storage medium.

4. The imaging apparatus according to claim 1, further comprising:
   display means capable of performing image display using the image data stored in said temporary storage means.

5. The imaging apparatus according to claim 4, wherein said display means is capable of causing a whole or a part of a screen area for image display to enter a transparent or translucent see-through state.

6. The imaging apparatus according to claim 5, wherein said control means controls said display means to cause part of the screen area for image display to enter the translucent see-through state, while performing image display using the image data stored in said temporary storage means with a remaining part of the screen area.

7. The imaging apparatus according to claim 5, wherein said control means controls said display means to perform image display using the image data being obtained by imaging by said imaging means with part of the screen area for image display, while performing image display using the image data stored in said temporary storage means with a remaining part of the screen area.

8. The imaging apparatus according to claim 4, wherein said display means is arranged in front of an eye of the user to perform image display.

9. The imaging apparatus according to claim 4, further comprising:
   operation input means;
   wherein in accordance with an operation input by the user detected by said operation input means, said control means controls said display means to perform image display using the image data stored in said temporary storage means.

10. The imaging apparatus according to claim 9, wherein said operation input means includes an operation unit to be operated by the user.

11. The imaging apparatus according to claim 9, wherein said operation input means includes a sensor for detecting a motion of the user.

12. The imaging apparatus according to claim 9, wherein said operation input means includes a sensor for detecting biological information representative of a user action.

13. The imaging apparatus according to claim 4, wherein, when said display means has performed image display using the image data stored in said temporary storage means, said control means determines that the at least one predetermined storage condition has been satisfied, and extracts, as the selected image data to be stored, all or some of the image data displayed from said temporary storage means and adds the metadata to the selected image data for storage.

14. The imaging apparatus according to claim 1, further comprising:
   biological sensor means for detecting biological trigger information representative of a user response to a scene;
   wherein said control means determines based on the biological trigger information detected by said biological sensor means whether the at least one predetermined storage condition has been satisfied, and when said control means has determined that the at least one predetermined storage condition has been satisfied, said control means extracts the selected image data to be stored from said temporary storage means and adds the metadata to the selected image data for storage.

15. The imaging apparatus according to claim 14, wherein the biological trigger information is at least one of a pulse, heart beats, an electrocardiogram, electromyographic information, breathing, perspiration, galvanic skin response, blood pressure, a saturation oxygen concentration in blood, a skin surface temperature, brain waves, a blood flow change, a body temperature, a motion of a body, a motion of a head, a center of gravity, rhythm of walking/running, and a state of an eye.

16. The imaging apparatus according to claim 1, further comprising:
   audio input means for inputting external sound; and
   audio analysis means for analyzing an audio signal obtained by said audio input means;
   wherein said control means determines based on a result of analysis by said audio analysis means whether the at least one predetermined storage condition has been satisfied, and when said control means has determined that the at least one predetermined storage condition has been satisfied, said control means extracts the selected image data to be stored from said temporary storage means and adds the metadata to the selected image data for storage.

17. The imaging apparatus according to claim 1, wherein said control means performs imaging system control of issuing an instruction related to imaging by said imaging means or processing on the image data obtained by imaging, and when said control means has performed imaging system control, said control means determines that the at least one predetermined storage condition has been satisfied, and extracts the selected image data to be stored from said temporary storage means and adds the metadata to the selected image data for storage.

18. The imaging apparatus according to claim 17, wherein said control means determines that the at least one predetermined storage condition has been satisfied when, as the imaging system control, said control means has performed control of causing a lens system in said imaging means to perform a predetermined operation.

19. The imaging apparatus according to claim 17, wherein said control means determines that the at least one predetermined storage condition has been satisfied when, as the imaging system control, said control means has performed control of causing a signal processing system in said imaging means to perform a predetermined process.

20. The imaging apparatus according to claim 17, wherein said control means determines that the at least one predetermined storage condition has been satisfied when, as the imaging system control, said control means has performed control of changing imaging sensitivity in said imaging means.

21. The imaging apparatus according to claim 17, wherein said control means determines that the at least one predetermined storage condition has been satisfied when, as the imaging system control, said control means has performed control of changing a frame rate in said imaging means.

22. The imaging apparatus according to claim 1, wherein, when the at least one predetermined storage condition has been satisfied, said control means generates the metadata in accordance with the at least one predetermined storage condition.

23. An imaging method of operating an imaging apparatus worn by a user, the method comprising acts of:
   (a) imaging at least one scene that is in a forward direction in which a user sees to obtain image data of the at least one scene;
   (b) continuously storing in temporary storage the image data using a storage area in a ring memory manner;
   (c) determining whether at least one predetermined storage condition of a plurality of predetermined storage conditions has been satisfied;
   (d) responsive to determining in step (c) that the predetermined storage condition has been satisfied, automatically extracting selected image data for storage in semi-permanent storage from the image data temporarily stored in step (b), and adding metadata to the extracted image data, wherein the metadata includes information about the at least one predetermined storage condition that caused the extraction and storage of the selected image data; and
   (e) executing a selected imaging operation from a plurality of active imaging operations responsive to detecting with an acceleration sensor a tapping pattern corresponding to the selected imaging operation applied by a user to the imaging apparatus, wherein the imaging apparatus comprises one rigid, head-wearable unit substantially in the shape of eye glasses that includes the acceleration sensor.

24. The imaging method according to claim 23, wherein in step (b), the image data is stored beginning at a start address, moving sequentially to an end address, and returning to the start address cyclically.

25. The imaging method according to claim 23, wherein step (d) further comprises storing the selected image data and the metadata in a nonvolatile storage medium.

26. The imaging method according to claim 23, wherein in step (d), the image data to be stored and the metadata are transmitted to an external device.

27. The imaging method according to claim 23, further comprising the step of:
   (f) performing image display using the image data temporarily stored in step (b).

28. The imaging method according to claim 27, wherein in step (f), a whole or a part of a screen area for image display is caused to enter a transparent or translucent see-through state.

29. The imaging method according to claim 28, wherein in step (f), part of the screen area for image display is caused to enter the translucent see-through state, while image display is performed using the image data temporarily stored in step (b) with a remaining part of the screen area.

30. The imaging method according to claim 27, wherein in step (f), image display is performed using image data being obtained by imaging by imaging means with part of the screen area for image display, while image display is performed using the image data temporarily stored in step (b) with a remaining part of the screen area.

31. The imaging method according to claim 27, wherein in step (f), image display is performed using the image data temporarily stored in step (b) in accordance with an operation input by the user detected by an operation input means.

32. The imaging method according to claim 27, wherein step (c) determines that the at least one predetermined storage condition has been satisfied when image display has been performed in step (f) using the image data temporarily stored in step (b), and in step (d), all or some of the image data displayed in step (f) is stored together with the added metadata.

33. The imaging method according to claim 23, wherein step (c) determines whether the at least one predetermined storage condition has been satisfied based on biological information detected by biological sensor means and associated with a user, and when step (c) has determined that the at least one predetermined storage condition has been satisfied, step (d) adds the metadata to the selected image data for storage.

34. The imaging method according to claim 23, wherein step (c) determines whether the at least one predetermined storage condition has been satisfied based on a result of analysis performed by an audio analysis means on an audio signal obtained by an audio input means, and when step (c) has determined that the at least one predetermined storage condition has been satisfied, step (d) adds the metadata to the selected image data for storage.

35. The imaging method according to claim 23, wherein step (c) determines that the at least one predetermined storage condition has been satisfied when a predetermined imaging system control of issuing an instruction related to imaging or processing on the image data obtained by imaging has been performed, and step (d) accordingly extracts the selected image data to be stored from the image data temporarily stored in step (b), adds the metadata to the selected image data, and performs a storage process.

36. The imaging method according to claim 35, wherein step (c) determines that the at least one predetermined storage condition has been satisfied when control of causing a lens system in an imaging means to perform a predetermined operation has been performed.

37. The imaging method according to claim 35, wherein step (c) determines that the at least one predetermined storage condition has been satisfied when control of causing a signal processing system in an imaging means to perform a predetermined process has been performed.

38. The imaging method according to claim 35, wherein step (c) determines that the at least one predetermined storage condition has been satisfied when control of changing imaging sensitivity in an imaging means has been performed.

39. The imaging method according to claim 35, wherein step (c) determines that the at least one predetermined storage condition has been satisfied when control of changing a frame rate in imaging means has been performed as an imaging system control.

40. The imaging method according to claim 23, further comprising the step of:
(g) when the at least one predetermined storage condition has been satisfied, generating the metadata in accordance with the at least one predetermined storage condition.

41. An imaging apparatus, comprising:
one rigid, head-wearable unit substantially in the shape of eye glasses that includes an acceleration sensor;
an imaging section having a camera configured to image at least one scene that is in a forward direction in which a user sees to obtain image data of the at least one scene;
a temporary storage section configured to store the image data continuously in a ring memory manner by beginning at a start address, moving sequentially to an end address, and returning to the start address cyclically; and
a control section configured to, when at least one predetermined trigger condition of a plurality of predetermined trigger conditions has been satisfied, automatically extract selected image data from the image data stored in temporary storage section for subsequent storage and associate metadata with the selected image data wherein the metadata includes information about the at least one predetermined trigger condition that caused the extraction and storage of the selected image data,
wherein the control section is further configured to execute a selected imaging operation from a plurality of active imaging operations responsive to detecting with the acceleration sensor a tapping pattern corresponding to the selected imaging operation applied by a user to the head-wearable unit imaging apparatus.

42. The imaging apparatus of claim 41, wherein the control section is further configured to execute a specific operation responsive to detecting a number of times the imaging apparatus is tapped.

43. The imaging apparatus of claim 41, wherein the control section is further configured to:
determine whether a left side or a right side of the imaging apparatus has been tapped;
execute a first action if the left side of the imaging apparatus has been tapped; and
execute a second action different from the first action if the right side of the imaging apparatus has been tapped.

* * * * *